(12) United States Patent
Shimizu

(10) Patent No.: US 12,060,322 B2
(45) Date of Patent: Aug. 13, 2024

(54) METHOD FOR PRODUCING ACETIC ACID

(71) Applicant: DAICEL CORPORATION, Osaka (JP)

(72) Inventor: Masahiko Shimizu, Himeji (JP)

(73) Assignee: DAICEL CORPORATION, Osaka (JP)

( * ) Notice: Subject to any disclaimer, the term of this patent is extended or adjusted under 35 U.S.C. 154(b) by 859 days.

(21) Appl. No.: 17/257,130

(22) PCT Filed: Jul. 2, 2018

(86) PCT No.: PCT/JP2018/025076
§ 371 (c)(1),
(2) Date: Dec. 30, 2020

(87) PCT Pub. No.: WO2020/008505
PCT Pub. Date: Jan. 9, 2020

(65) Prior Publication Data
US 2021/0122694 A1    Apr. 29, 2021

(51) Int. Cl.
*C07C 51/44*         (2006.01)
*B01D 3/38*          (2006.01)
(Continued)

(52) U.S. Cl.
CPC .............. *C07C 51/445* (2013.01); *B01D 3/38* (2013.01); *B01D 53/1406* (2013.01);
(Continued)

(58) Field of Classification Search
None
See application file for complete search history.

(56) References Cited

U.S. PATENT DOCUMENTS 9,233,907 B1   1/2016  Shaver et al.
9,458,077 B2  10/2016  Shaver et al.
(Continued)

FOREIGN PATENT DOCUMENTS

CN   1651388 A      8/2005
CN   1325459 C  *   7/2007
(Continued)

OTHER PUBLICATIONS

Chinese Office Action and Search Report for Chinese Application No. 201880095243.4, dated Apr. 24, 2023.
(Continued)

*Primary Examiner* — Amy C Bonaparte
(74) *Attorney, Agent, or Firm* — Birch, Stewart, Kolasch & Birch, LLP

(57) ABSTRACT

A method for producing acetic acid includes an absorption step that suppresses corrosion inside a distillation column when a solution after that has absorbed a target component is subjected to distillation. The method for producing acetic acid also includes an absorption step of supplying, to an absorption column, at least a portion of offgas generated in an acetic acid production process, bringing the offgas into contact with an absorbent containing one or more liquids selected from a hydrocarbon, an ester of a carboxylic acid having 3 or more carbon atoms, an ester of a carboxylic acid and an alcohol having 2 or more carbon atoms, and an ether, to allow the absorbent to absorb an iodine compound in the offgas, and separating into a gas component having a lower iodine compound concentration than the offgas and a solution containing the absorbent and the iodine compound.

14 Claims, 11 Drawing Sheets

(51) Int. Cl.
*B01D 53/14* (2006.01)
*C07C 51/12* (2006.01)
(52) U.S. Cl.
CPC ..... *B01D 53/1425* (2013.01); *B01D 53/1431* (2013.01); *B01D 53/1493* (2013.01); *C07C 51/12* (2013.01); *B01D 2252/103* (2013.01); *B01D 2252/205* (2013.01)

(56) References Cited

U.S. PATENT DOCUMENTS

| | | | |
|---|---|---|---|
| 10,428,006 B2 | 10/2019 | Miura et al. | |
| 10,759,730 B2 * | 9/2020 | Shimizu | B01D 3/143 |
| 10,894,759 B2 | 1/2021 | Miura et al. | |
| 2009/0270651 A1 * | 10/2009 | Zinobile | C07C 51/12 422/198 |
| 2016/0137574 A1 | 5/2016 | Shaver et al. | |
| 2018/0230077 A1 | 8/2018 | Miura et al. | |
| 2019/0367439 A1 | 12/2019 | Miura et al. | |

FOREIGN PATENT DOCUMENTS

| | | | |
|---|---|---|---|
| CN | 107108440 A | | 8/2017 |
| JP | 9-235250 A | | 9/1997 |
| JP | H09235250 A | * | 9/1997 |
| JP | 2018-121126 A | | 7/2016 |
| WO | WO 2017/057142 A1 | | 4/2017 |

OTHER PUBLICATIONS

International Preliminary Report on Patentability and Written Opinion of the International Searching Authority with an English translation, dated Jan. 5, 2021, for International Application No. PCT/JP2018/025076.

International Search Report, dated Jul. 31, 2018, for International Application No. PCT/JP2018/025076, with an English translation.

* cited by examiner

METHOD FOR PRODUCING ACETIC ACID

TECHNICAL FIELD

The present invention relates to a method for producing acetic acid.

BACKGROUND ART

As an industrial production method of acetic acid, a methanol carbonylation process (methanol-acetic acid process) is known. In this process, for example, methanol is reacted with carbon monoxide in the presence of a catalyst in a reactor to form acetic acid, the resulting reaction mixture is subjected to evaporation in an evaporator to give a vapor phase, the vapor phase is purified through a low-boiling component-removing column and subsequently through a dehydration column to give an acetic acid product, or further purified through a high-boiling component-removing column subsequent to the dehydration column, and, further, through a product column to give an acetic acid product.

In the acetic acid production process as above, an offgas from a process typically using a reaction system or a purification system includes useful components (such as methyl iodide, water, methyl acetate, and acetic acid). Before discarding of the offgas, the useful components are recovered from the offgas typically by absorption treatment with an absorbing solvent in a scrubber system.

Patent Literature 1 discloses an acetic acid production method in which a specific process stream is brought into contact with a first absorbent selected from the group consisting of acetic acid, methanol, and methyl acetate, or further brought into contact with a second absorbent including at least one of methanol and methyl acetate.

CITATION LIST

Patent Document

Patent Document 1: JP 2016-121126 A

SUMMARY OF INVENTION

Technical Problem

The resulting solution after absorption of such useful components is then supplied to a distillation column and is separated, by distillation, into the useful components and the absorbing solvent. By the distillation, the useful components such as methyl iodide are generally concentrated in an overhead stream from the distillation column, and the concentrated methyl iodide can be recycled to the reactor and reused in the reaction step.

However, disadvantageously, in the method disclosed in Patent Document 1, in a case where acetic acid, methanol, or methyl acetate is used as an absorbing solvent, which is high in polarity and susceptible to acid dissociation, an interior of the distillation column is prone to corrosion, when the solution after absorbing useful components is subjected to distillation and separated.

Therefore, an object of the present invention is to provide a method for producing acetic acid, including an absorption step in which corrosion of the interior of the distillation column is suppressed when the solution after absorbing the target component is subjected to distillation.

Solution to Problem

In order to achieve the above object, the present inventors studied diligently with a focus on the polarity of the absorbing solvent. As a result, the present inventors discovered that use of a solvent having low polarity as an absorbing solvent can suppress corrosion inside the distillation column in the subsequent distillation step. The present invention has been completed by further studying based on these findings.

That is, the present invention provides a method for producing acetic acid, including an absorption step of supplying, to an absorption column, at least a portion of offgas formed in an acetic acid production process, and bringing the offgas into contact with an absorbent containing one or more liquids selected from the group consisting of a hydrocarbon, an ester of a carboxylic acid having 3 or more carbon atoms, an ester of a carboxylic acid and an alcohol having 2 or more carbon atoms, and an ether, to allow the absorbent to absorb an iodine compound in the offgas, and separating into a gas component having a lower iodine compound concentration than the offgas and a solution containing the absorbent and the iodine compound.

The present invention also provides method for producing acetic acid, the method including:
  a carbonylation reaction step of reacting methanol with carbon monoxide in the presence of a catalytic system containing a metal catalyst and methyl iodide, acetic acid, methyl acetate, and water in a reactor to form acetic acid;
  a separation step of separating, using at least one selected from evaporators and distillation columns, a reaction mixture from the carbonylation reaction step into:
  a stream including a metal catalyst;
  an acetic acid stream rich in acetic acid; and
  a stream richer in a low boiling component than the acetic acid stream,
  the method optionally further including an acetaldehyde separation and removal system that is configured to separate, using a distillation column or columns, acetaldehyde from at least a portion of a condensed liquid resulting from condensing the stream rich in a low boiling component,
  the method including
  an absorption step of:
  supplying, to the absorption column, one or more offgas selected from the group consisting of:
  an exhaust gas from the reactor;
  an exhaust gas from the evaporator or evaporators;
  an exhaust gas from the distillation column or columns in the separation step; and
  an exhaust gas from the distillation column or columns in the acetaldehyde separation and removal system;
  bringing the offgas into contact with an absorbent containing one or more liquids selected from the group consisting of a hydrocarbon, an ester of a carboxylic acid having 3 or more carbon atoms, an ester of a carboxylic acid and an alcohol having 2 or more carbon atoms, and an ether to allow the absorbent to absorb an iodine compound in the offgas, and
  whereby separating into:
  a gas component having a lower iodine compound concentration than the offgas; and
  a solution containing the absorbent and the iodine compound.

The present invention also provides a method for producing acetic acid, including:

a carbonylation reaction step of reacting methanol and carbon monoxide in a reactor in the presence of a catalytic system, acetic acid, methyl acetate, and water to form acetic acid, the catalytic system including a metal catalyst and methyl iodide;

an evaporation step of separating, using an evaporator, a reaction mixture from the carbonylation reaction step into:

a vapor stream; and a residual liquid stream;

a low-boiling component-removing step of subjecting the vapor stream to distillation and separating the vapor stream into:

an overhead stream rich in a low boiling component; and a first acetic acid stream rich in acetic acid; and a dehydration step of subjecting the first acetic acid stream to distillation and separating the first acetic acid stream into:

an overhead stream rich in water; and a second acetic acid stream richer in acetic acid than the first acetic acid stream, the method optionally further including:

a high-boiling component-removing step of distilling the second acetic acid stream and separating the second acetic acid stream into:

a bottoms stream rich in high boiling components; and a third acetic acid stream richer in acetic acid than the acetic acid stream before being subjected to the distillation; and an acetaldehyde separation and removal system that is configured to separate, using a distillation column or columns, acetaldehyde from at least a portion of a condensed liquid resulting from condensing the stream rich in a low boiling component, the method including:

an absorption step of supplying, to the absorption column, one or more offgas selected from the group consisting of:

an exhaust gas from the reactor;

an exhaust gas from the evaporator;

an exhaust gas from the distillation column in the low-boiling component-removing step;

an exhaust gas from the distillation column in the dehydration step;

an exhaust gas from the distillation column in the high-boiling component-removing step; and an exhaust gas from the distillation column in the acetaldehyde separation and removal system, bringing the offgas into contact with an absorbent containing one or more liquids selected from the group consisting of a hydrocarbon, an ester of a carboxylic acid having 3 or more carbon atoms, an ester of a carboxylic acid and an alcohol having 2 or more carbon atoms, and an ether to allow the absorbent to absorb an iodine compound in the offgas, and whereby separating into:

a gas component having a lower iodine compound concentration than the offgas; and a solution containing the absorbent and the iodine compound.

In the absorbent, the concentration of one or more liquids selected from the group consisting of a hydrocarbon, an ester of a carboxylic acid having 3 or more carbon atoms, an ester of a carboxylic acid and an alcohol having 2 or more carbon atoms, and an ether is preferably 10 ppm by mass or more. The absorbent preferably contains a hydrocarbon.

The acetic acid production process includes:

a first absorption step of supplying at least a portion of offgas formed in the process to an absorption column and bringing the portion of the offgas into contact with a first absorbent to allow the first absorbent to absorb an iodine compound in the offgas, and separating into:

a first gas component having a lower iodine compound concentration than the offgas; and a first solution containing the first absorbent and the iodine compound; and a second absorption step of, in an absorption column, bringing the first gas component into contact with a second absorbent to allow the second absorbent to absorb an iodine compound in the first gas component, the second absorbent having a composition different from that of the first absorbent, and separating into:

a second gas component having a lower iodine compound concentration than the first gas component; and a second solution containing the second absorbent and an iodine compound, and the method preferably includes, as the first absorption step and/or the second absorption step, the absorption step using an absorbent containing one or more liquids selected from the group consisting of a hydrocarbon, an ester of a carboxylic acid having 3 or more carbon atoms, an ester of a carboxylic acid and an alcohol having 2 or more carbon atoms, and an ether.

The first absorbent preferably contains water.

The second absorption step is preferably the absorption step using an absorbent containing one or more liquids selected from the group consisting of a hydrocarbon, an ester of a carboxylic acid having 3 or more carbon atoms, an ester of a carboxylic acid and an alcohol having 2 or more carbon atoms, and an ether.

The water concentration in the first or second absorbent may be 10 ppm by mass or greater.

In the first absorbent and the second absorbent, a water concentration in one of the first absorbent and the second absorbent is 10 ppm by mass or greater, and a concentration of one or more liquids selected from the group consisting of a hydrocarbon, an ester of a carboxylic acid having 3 or more carbon atoms, an ester of a carboxylic acid and an alcohol having 2 or more carbon atoms, and an ether in the other one of the first absorbent and the second absorbent is 10 ppm by mass or greater.

The first absorption step and the second absorption step may be performed using different absorption columns.

The method may include a stripping step of subjecting a solution containing an absorbent and an iodine compound to distillation, the absorbent containing one or more liquids selected from the group consisting of a hydrocarbon, an ester of a carboxylic acid having 3 or more carbon atoms, an ester of a carboxylic acid and an alcohol having 2 or more carbon atoms, and an ether, and separating into:

an overhead stream rich in methyl iodide; and a bottoms stream rich in the liquid.

The overhead stream rich in methyl iodide may be recycled to one or more steps selected from the group consisting of the reaction step, the evaporation step, and the distillation step.

A methyl iodide concentration in a charge liquid to the distillation column in the stripping step is preferably 1 ppm by mass or greater.

A hydrogen iodide concentration in the charge liquid in the distillation column in the stripping step is preferably less than 1 mass %.

Advantageous Effects of Invention

According to the present invention, in the absorption step, use of one or more liquids selected from the group consisting of a hydrocarbon, an ester of a carboxylic acid having 3 or more carbon atoms, an ester of a carboxylic acid and an alcohol having 2 or more carbon atoms, and an ether as an absorbent, can suppress corrosion inside the distillation column in the subsequent distillation step compared to the case where acetic acid, methanol, or methyl acetate is used.

DESCRIPTION OF EMBODIMENTS

Figure 1:
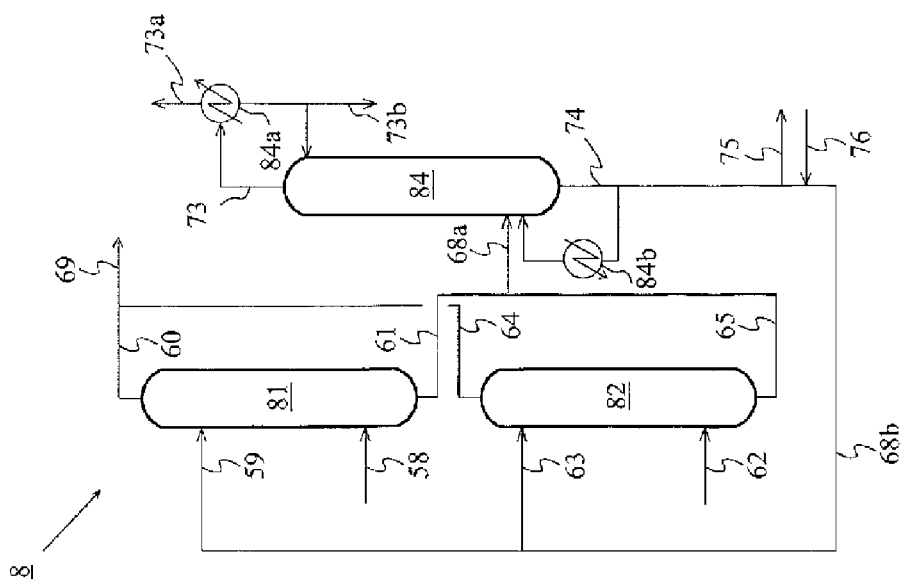
FIG. 1 is a schematic flow chart illustrating an example of a scrubber system.

The method for producing acetic acid according to an embodiment of the present invention includes an absorption step of supplying, to an absorption column, at least a portion of offgas generated in an acetic acid production process, bringing the offgas into contact with an absorbent containing one or more liquids selected from the group consisting of a hydrocarbon, an ester of a carboxylic acid having 3 or more carbon atoms, an ester of a carboxylic acid and an alcohol having 2 or more carbon atoms, and an ether, to allow the absorbent to absorb an iodine compound in the offgas, and separating into a gas component having a lower iodine compound concentration than the offgas and a solution containing the absorbent and the iodine compound. Note that, in this specification, the absorption step may be referred to as "the absorption step of the present invention".

In the method for producing acetic acid according to an embodiment of the present invention, at least a portion of all the offgas generated in the acetic acid production process is directly or indirectly supplied to the absorption column and subjected to the absorption step according to an embodiment of the present invention. Examples of the offgas subjected to the absorption step according to an embodiment of the present invention include an exhaust gas from a reactor in a reaction step described later, an exhaust gas from an evaporator in an evaporation step, an exhaust gas from a distillation column in a separation step, and an exhaust gas from a distillation column in an acetaldehyde separation and removal system.

The absorption step according to the present invention is the step of bringing an offgas formed in the process into contact (in particular, countercurrent contact) with an absorbent to allow the absorbent to absorb an iodine compound from the offgas and whereby separating the offgas into a gas component and a solution, where the gas component has a lower iodine compound concentration than the offgas, and the solution contains the absorbent and the iodine compound. Specifically, the offgas is continuously introduced into an absorption column with which the absorption step is performed; whereas the absorbent is continuously introduced into the absorption column through a line provided at a higher position in the absorption column than a position at which the offgas is supplied. In the column, the offgas traveling upward and the absorbent traveling downward are brought into countercurrent contact with each other to allow the absorbent to absorb an iodine compound from the offgas. Thus, a gas component having a lower iodine compound concentration than the offgas, and a solution containing the iodine compound and the absorbent are to be separated.

The absorption step according to an embodiment of the present invention may be performed in one absorption column or in two or more absorption columns. For example, in a case where offgases from two or more processes are subjected to the absorption step, because the offgases have different component compositions and pressures, the absorption step may be performed by an adsorption method using two or more absorption columns (for example, a high-pressure absorption column and a low-pressure absorption column). For example, when it is desired to efficiently separate two or more iodine compounds from the offgas, in the absorption step, two or more absorption columns may be arranged in series, and an absorbent used in each absorption column may have a different composition from one another such that each absorption column may absorb different iodine compound.

Examples of the iodine compound to be absorbed by the absorbent in the absorption step according to an embodiment of the present invention include iodine compounds present in the process, such as hydrogen iodide; and alkyl iodide such as methyl iodide, ethyl iodide, and hexyl iodide. Among them, an iodine compound to be absorbed by the absorbent is preferably hydrogen iodide, which may corrode the inside of the distillation column, and methyl iodide, which is a useful component that can be used in the reaction step. When hydrogen iodide is absorbed in the absorption step, the concentration of hydrogen iodide in the gas component becomes extremely low. And when a further absorption step is provided downstream, corrosion inside the absorption column, in which the absorption step is performed, is unlikely to occur. Furthermore, corrosion inside the distillation column, in which the solution is distilled in the stripping step described later, is unlikely to occur. Thus, a low-grade material can be used for the absorption column and the distillation column. When methyl iodide is absorbed in the absorption step, methyl iodide can be separated and obtained by distilling the above solution in the stripping step described later, and recycled to a reactor to reuse methyl iodide in the reaction step. Only one kind of the iodine compound or two or more kinds of the iodine compounds may be absorbed in the absorption step.

In the absorption step according to an embodiment of the present invention, as an absorbent, one or more liquids selected from the group consisting of a hydrocarbon, an ester of a carboxylic acid having 3 or more carbon atoms, an ester of a carboxylic acid and an alcohol having 2 or more carbon atoms, and an ether is used. Since the above liquid has a relatively low polarity, when the solution obtained through the absorption step (solution containing methyl iodide and an absorbent) is subjected to distillation and methyl iodide is separated (stripping step described later), corrosion inside the distillation column can be suppressed compared to the case where acetic acid, methanol, or methyl acetate is used. The above liquid may contain only one kind of the absorbent, or may contain two or more kinds of the absorbents.

The hydrocarbon above is liquid at room temperature and has a higher boiling point than methyl iodide. Examples of the hydrocarbon include saturated or unsaturated aliphatic hydrocarbons, alicyclic hydrocarbons, and aromatic hydrocarbons. The aliphatic hydrocarbons may be either linear aliphatic hydrocarbons or branched chain hydrocarbons, and examples thereof include saturated aliphatic hydrocarbons having 5 or more carbon atoms (for example, 5 to 20 carbon atoms) such as pentane, hexane, heptane, and octane. Examples of the alicyclic hydrocarbons include alicyclic hydrocarbons having 5 or more carbon atoms (for example, 5 to 20 carbon atoms) such as cyclopentane, cyclohexane, and methylcyclohexane. Examples of the aromatic hydrocarbons include aromatic hydrocarbons having 6 or more carbon atoms (for example, 6 to 20 carbon atoms) such as benzene, toluene, and xylene.

Examples of the ester of the carboxylic acid having 3 or more carbon atoms include propionic acid esters such as methyl propionate and ethyl propionate; lactic acid esters such as methyl lactate and ethyl lactate; monocarboxylic acid esters including butyric acid esters such as methyl butyrate and ethyl butyrate, and dicarboxylic acid esters such as adipates.

Examples of the ester of the carboxylic acid and an alcohol having 2 or more carbon atoms include carboxylic acid ethyl esters such as ethyl acetate, ethyl propionate, ethyl lactate and ethyl butyrate; carboxylic acid propyl esters such as propyl acetate; alkylene glycol acetates such as ethylene glycol monoethyl ether acetate.

Examples of the ether include aliphatic ethers such as methyl ethyl ether, diethyl ether, ethylene glycol monoethyl ether, and ethylene glycol monobutyl ether; aromatic ethers such as diphenyl ether; cyclic ethers such as tetrahydrofuran; and alkylene glycol ether acetates such as ethylene glycol monoethyl ether acetate.

The liquid used in the absorbent is, from the viewpoint of having a lower polarity and suppressing corrosion of the distillation column, preferably a hydrocarbon, more preferably an aliphatic hydrocarbon, and even more preferably a saturated aliphatic hydrocarbon. In addition, from the viewpoint that the boiling point is relatively low and corrosion of the distillation column can be further suppressed, hydrocarbons having from 5 to 7 carbon atoms such as pentane, cyclopentane, methylcyclopentane, hexane, cyclohexane, benzene, heptane, methylcyclohexane, and toluene are preferable.

The absorbent may contain a component besides the liquid. Examples of such a component include alcohols such as methanol, esters of carboxylic acid having 1 or 2 carbon atoms such as methyl acetate, methyl esters of a carboxylic acid having 3 or more carbon atoms, carboxylic acids such as acetic acid and formic acid, ketones, liquids other than the above liquids such as water (including the case of alkaline aqueous solution); and other impurities used or formed in the acetic acid production process.

The concentration of one or more liquids selected from the group consisting of a hydrocarbon, an ester of a carboxylic acid having 3 or more carbon atoms, an ester of a carboxylic acid and an alcohol having 2 or more carbon atoms, and an ether in the absorbent is, for example, 10 ppm by mass or more, preferably 20 ppm by mass or more, more preferably 50 ppm by mass or more, even more preferably 100 ppm by mass or greater, and particularly preferably 200 ppm by mass or greater, and may be 300 ppm by mass or greater, 400 ppm by mass or greater, 500 ppm by mass or greater, 1000 ppm by mass or greater, 1 mass % or greater, 5 mass % or greater, 10 mass % or greater, 20 mass % or greater, 30 mass % or greater, 40 mass % or greater, 50 mass % or greater, 60 mass % or greater, 70 mass % or greater, 80 mass % or greater, and 90 mass % or greater. The upper limit of the above concentration is 100 mass %, but may be 99.999 mass %, 99.99 mass %, 99.9 mass %, 99.5 mass %, 99 mass %, or 98 mass %. The hydrocarbon concentration in the absorbent may be within the above range.

Hydrogen iodide contains both molecular hydrogen iodide and dissociated hydrogen iodide when at least partly ionized in a polar medium (usually at least a medium containing water), the two being compatible. In the present specification, a concentration of the hydrogen iodide may be determined by a potentiometric titration method or by a subtraction method, in which the concentration of the hydrogen iodide is determined by subtracting other iodides from total ionic iodide.

In the potentiometric titration method, the concentration is determined from the potentiometric titration end point in the acid-base titration. In particular, the hydrogen iodide concentration is determined by titrating to the end point of potentiometric titration using a standard lithium acetate solution or the like. The subtraction method is a method of determining the concentration of the hydrogen iodide by subtracting a concentration of iodides which are presumed to be related to the measurement of corrosion metals or other non-hydrogen cations, from the total ionic iodide present in the sample.

The hydrogen iodide concentration in the above solution determined by the subtraction method is, for example, 0.01 ppm by mass or greater, and may be 0.1 ppm by mass or greater, 1 ppm by mass or greater, 10 ppm by mass or greater, 50 ppm by mass or greater, 100 ppm by mass or greater, 200 ppm by mass or greater, 300 ppm by mass or greater, 400 ppm by mass or greater, 500 ppm by mass or greater, 600 ppm by mass or greater, 700 ppm by mass or greater, 800 ppm by mass or greater, 900 ppm by mass or greater, 1000 ppm by mass or greater, 2000 ppm by mass or greater, 3000 ppm by mass or greater, 4000 ppm by mass or greater, 5000 ppm by mass or greater, 6000 ppm by mass or greater, 7000 ppm by mass or greater, 8000 ppm by mass or greater, 9000 ppm by mass or greater, and 1 mass % or greater. The hydrogen iodide concentration is, for example, 10 mass % or less, and may be 5 mass % or less, 3 mass % or less, 2 mass % or less, 1 mass % or less, less than 1 mass %, 5000 ppm by mass or less, and 3000 ppm by mass or less.

The hydrogen iodide concentration in the above solution determined by the potentiometric titration method is, for example, 0.01 ppm by mass or greater, and may be 0.1 ppm by mass or greater, 1 ppm by mass or greater, 10 ppm by mass or greater, 50 ppm by mass or greater, 100 ppm by mass or greater, 200 ppm by mass or greater, 300 ppm by mass or greater, 400 ppm by mass or greater, 500 ppm by mass or greater, 600 ppm by mass or greater, 700 ppm by mass or greater, 800 ppm by mass or greater, 900 ppm by mass or greater, 1000 ppm by mass or greater, 2000 ppm by mass or greater, 3000 ppm by mass or greater, 4000 ppm by mass or greater, 5000 ppm by mass or greater, 6000 ppm by mass or greater, 7000 ppm by mass or greater, 8000 ppm by mass or greater, 9000 ppm by mass or greater, and 1 mass % or greater. The hydrogen iodide concentration is, for example, 5 mass % or less, and preferably 2 mass % or less. The hydrogen iodide concentration is, for example, 10 mass % or less, and may be 5 mass % or less, 3 mass % or less, 2 mass % or less, 1 mass % or less, less than 1 mass %, 5000 ppm by mass or less, and 3000 ppm by mass or less.

The methyl iodide concentration in the solution is, for example, and may be 1 ppm by mass or more, 10 ppm by mass or greater, 50 ppm by mass or greater, 100 ppm by mass or greater, 1000 ppm by mass or greater, 5000 ppm by mass or greater, and 1 mass % or greater. The methyl iodide concentration is, for example, 20 mass % or less (for example, 15 mass % or less), and preferably 10 mass % or less (for example, 8 mass % or less).

The method for producing acetic acid according to an embodiment of the present invention may include other absorption step besides the absorption step according to an embodiment of the present invention. The other absorption step is identical to the absorption step according to an embodiment of the present invention, except that a component other than one or more liquids selected from the group consisting of a hydrocarbon, an ester of a carboxylic acid having 3 or more carbon atoms, an ester of a carboxylic acid and an alcohol having 2 or more carbon atoms, and an ether is used as an absorbent.

The method for producing acetic acid according to an embodiment of the present invention may include a distillation step (stripping step) of subjecting the solution from the absorption step to distillation. In the stripping step, the solution is subjected to distillation, and an overhead stream richer in a low boiling component than the absorbent is separated from a bottoms stream rich in the absorbent. When the method of producing acetic acid includes the stripping step, the useful components can be separated from the bottoms stream rich in the absorbent, and the useful components can be recycled to the reactor and the separated absorbent can be reused as the absorbent in the absorption step; whereby improving economical aspects of the production.

The methyl iodide concentration in the charge liquid in the distillation column in the stripping step is, for example, 1 ppm by mass or greater, 10 ppm by mass or greater, 50 ppm by mass or greater, 100 ppm by mass or greater, 1000 ppm by mass or greater, 5000 ppm by mass or greater, and may be 1 mass % or greater. The methyl iodide concentration is, for example, 20 mass % or less (for example, 15 mass % or less), preferably 10 mass % or less (for example, 8 mass % or less).

The hydrogen iodide concentration in the charge liquid in the distillation column performing the stripping step, which is obtained by the subtraction method, is, for example, 5 mass % or less, and may be 4 mass % or less, 3 mass % or less, 2 mass % or less, 1 mass % or less, less than 1 mass %, 5000 ppm by mass or less, 3000 ppm by mass or less, 2000 ppm by mass or less, 1000 ppm by mass or less, 700 ppm by mass or less, 500 ppm by mass or less, 300 ppm by mass or less, 200 ppm by mass or less, 100 ppm by mass or less, less than 100 ppm by mass, 50 ppm by mass or less, 30 ppm by mass or less, 20 ppm by mass or less, 10 ppm by mass or less, 5 ppm by mass or less, 3 ppm by mass or less, 2 ppm by mass or less, and 1 ppm by mass or less. The hydrogen iodide concentration is, for example, 0.0001 ppm by mass or greater, and may be 0.001 ppm by mass or more, 0.01 ppm by mass or greater, 0.1 ppm by mass or greater, 0.5 ppm by mass or greater, and 1 ppm by mass or greater.

The hydrogen iodide concentration in the charge liquid in the distillation column performing the stripping step, which is determined by the potentiometric titration method, is, for example, 5 mass % or less, and may be 4 mass % or less, 3 mass % or less, 2 mass % or less, 1 mass % or less, less than 1 mass %, 5000 ppm by mass or less, 3000 ppm by mass or less, 2000 ppm by mass or less, 1000 ppm by mass or less, 700 ppm by mass or less, 500 ppm by mass or less, 300 ppm by mass or less, 200 ppm by mass or less, 100 ppm by mass or less, less than 100 ppm by mass, 50 ppm by mass or less, 30 ppm by mass or less, 20 ppm by mass or less, 10 ppm by mass or less, 5 ppm by mass or less, 3 ppm by mass or less, 2 ppm by mass or less, and 1 ppm by mass or less. The hydrogen iodide concentration is, for example, 0.0001 ppm by mass or greater, and may be 0.001 ppm by mass or greater, 0.01 ppm by mass or greater, 0.1 ppm by mass or greater, 0.5 ppm by mass or greater, and 1 ppm by mass or greater.

Examples of the low boiling component concentrated in the overhead stream separated and obtained in the stripping step include iodine compounds (methyl iodide, hydrogen iodide, etc.), water, methyl acetate, dimethyl ether, methanol, acetaldehyde, and formic acid. When the overhead stream contains useful components such as methyl iodide, at least a portion of it may be recycled to the reactor (reaction step). Recycling to the reactor enables the reuse of useful components in the reaction step, whereby improving economical aspects of production. Further, the overhead stream may be recycled to a distillation step (for example, low-boiling component-removing step, dehydration step, or high-boiling component-removing step) which is provided downstream of the evaporation step.

When the offgas subjected to the absorption step is an exhaust gas from the decanter configured to store the condensed liquid from condensation of an overhead stream from the low-boiling component-removing step described later, an overhead stream from the stripping step may contain a large amount of acetaldehyde Therefore, the overhead stream from the stripping step may be supplied to the acetaldehyde separation and removal system, and acetaldehyde may be removed by the acetaldehyde separation and removal system and then recycled to the reactor through a decanter.

A methyl iodide concentration in the overhead stream from the stripping step is, for example, 5 mass % or greater, and may be 10 mass % or greater, 20 mass % or greater, 30 mass % or greater, 40 mass % or greater, 50 mass % or greater, 60 mass % or greater, 70 mass % or greater, and 80 mass % or greater. An upper limit of the methyl iodide concentration is, for example, 99.9 mass % (for example, 99 mass %), preferably 98 mass % (for example, 95 mass %), more preferably 93 mass % (90 mass %), and may be 80 mass %, 70 mass %, 60 mass %, 50 mass %, and 45 mass %.

At least a portion of a bottoms stream from a bottom of the distillation column, which is separated and acquired in the stripping step, may be continuously discharged out of the system, or at least a portion may be circulated to the absorption column. At least a portion of the bottoms stream may be recycled to a reaction step, an evaporation step, a purification step downstream of the evaporation step, and the like.

Hereinafter, an embodiment of a scrubber system including the absorption step according to an embodiment of the present invention will be described. FIG. 1 is an example of a schematic flow chart illustrating an embodiment of the scrubber system in the present invention. The scrubber system 8 includes an absorption column 81, an absorption column 82, and a distillation column 84. In the method for producing acetic acid of the present embodiment, an absorption step is performed in the absorption columns 81 and 82, and a stripping step is performed in the distillation column 84, respectively. The absorption step according to an embodiment of the present invention is performed in at least one of the absorption columns 81 and 82, preferably both. The absorbents used in the absorption columns may be the same or different.

The absorption column 81 is a unit (high-pressure absorption column), in which an absorption step of absorbing and recovering an iodine compound from the high-pressure gas of the offgas is performed. In this absorption step, a high-pressure gas is brought into contact with an absorbent to allow the absorbent to absorb the iodine compound in the high-pressure gas, and a gas component having a lower iodine compound concentration than the high-pressure gas is separated from a solution containing an absorbent and an iodine compound.

Specifically, the high-pressure gas is continuously introduced into the absorption column 81 through a line 58 (high-pressure gas supply line), while an absorbent is continuously introduced into the absorption column 81 through a line 59 (absorbent supply line) located at a position higher than a position where the high-pressure gas is introduced. Thus, the high-pressure gas traveling upward and the absorbent traveling downward in the column are brought into countercurrent contact, and the iodine compound in the high-pressure gas is absorbed by the absorbent. Then, the gas component having a lower iodine compound concentration than the high-pressure gas and the solution containing the iodine compound and the absorbent are separated, and the gas component is obtained from the top of the absorption column 81 through a line 60, and the solution is obtained from the bottom of the absorption column 81 through a line 61.

The high-pressure gas is, for example, an exhaust gas from the reactor (or reaction step). The exhaust gas discharged from the reactor may be directly supplied to the absorption column 81 through the line 58. Alternatively, a condensed component of the exhaust gas discharged from the reactor may be separated by a condenser, and the resultant non-condensable gas may be supplied to the absorption column 81 through the line 58. The temperature of the absorbent before being supplied to the absorption column 81 is, for example, from 1 to 120° C. In this temperature range, the absorbent does not freeze and does not boil.

The absorption column 81 includes a rectification column such as a plate column and a packed column. The packing in the packed column may be either a structured packing or a random packing. When a plate column is adopted, the theoretical number of plates is, for example, from 1 to 100. The pressure inside the column is, for example, atmospheric pressure to 5 MPaG (gauge pressure), which is usually equal to or lower than the pressure inside the reactor. The temperature inside the column is, for example, about 1 to 120° C.

The absorption column 82 is a unit configured to perform an absorption step of absorbing and recovering an iodine compound from the low-pressure gas of the offgases (low-pressure absorption column). In this absorption step, a low-pressure gas is brought into contact with an absorbent to allow the absorbent to absorb the iodine compound in the low-pressure gas, and a gas component having a lower iodine compound concentration than the low-pressure gas is separated from a solution containing an absorbent and an iodine compound.

Specifically, a low-pressure gas is continuously introduced into the absorption column 82 through a line 62 (low-pressure gas supply line), while the absorbent is continuously introduced into the absorption column 82 through a line 63 (absorbent supply line) located at a position higher than a position where the low-pressure gas is introduced. Thus, the low-pressure gas traveling upward and the absorbent traveling downward in the column are brought into countercurrent contact, and the iodine compound in the low-pressure gas is absorbed by the absorbent. Then, the gas component having a lower iodine compound concentration than the low-pressure gas and the solution containing the iodine compound and the absorbent are separated, and the gas component is obtained from the top of the absorption column 82 through a line 64, and the solution is obtained from the bottom of the absorption column 82 through a line 65.

Examples of the low-pressure gas include an exhaust gas from the evaporator (or evaporation step), an exhaust gas from the low-boiling component-removing column (or low-boiling component-removing step), an exhaust gas from the decanter configured to store the condensed liquid resulting from condensing the overhead stream rich in a low boiling component from the low-boiling component-removing column, an exhaust gas from the dehydration column (or dehydration step), and exhaust gas from the high-boiling component-removing column (or high-boiling component-removing step). These exhaust gases may be directly supplied to the absorption column 82 through the line 62, or may be supplied to the absorption column 82 through the line 62 as non-condensable gas whose condensed component is separated by a condenser. The temperature of the absorbent before being supplied to the absorption column 82 is the same as the temperature of the absorbent before being supplied to the absorption column 81.

The gas component from the top of the absorption column 81 (line 60) and the gas component from the top of the absorption column 82 (line 64) are gases in which useful components and hydrogen iodide have been collected and removed, and these gas components are merged and discarded through a line 69. The gas discharged from each of the line 69 or the lines 60 and 64 before merging may be used as a CO source to be introduced into the bottom of the evaporator 2 or residual liquid stream recycling lines 18 and 19 described later. On the other hand, the solution from the bottom of the absorption column 81 (line 61) and the solution from the bottom of the absorption column 82 (line 65) are merged and supplied to the distillation column 84 through a line 68a.

The distillation column 84 is a unit configured to perform a stripping step. In the stripping step in the present embodiment, the solution from the bottom of the absorption column (line 68a) is subjected to distillation to be separated into an overhead stream rich in useful components (particularly methyl iodide) and a bottoms stream rich in the absorbent. More specifically, the solution which is continuously introduced into the distillation column 84 (line 68a) is subjected to distillation to be separated into an overhead stream rich in useful components (particularly methyl iodide) and a bottoms liquid rich in the absorbent. From the top of the distillation column 84, vapor, which is an overhead stream, is continuously drawn into a line 73. From the bottom of the distillation column 84, a bottoms liquid is continuously drawn into a line 74. 84b indicates a reboiler.

The distillation column 84 includes, for example, a rectification column such as a plate column and a packed column. The overhead stream of the distillation column 84 is introduced into a condenser 84a through the line 73. The condenser 84a cools and partially condenses the overhead stream from the distillation column 84 to separate the overhead stream into the condensed component and the gas component. A portion of the condensed component is refluxed to the distillation column 84, and another portion is distilled out through a line 73b. Although FIG. 1 illustrates an example in which the condensed component is refluxed to the distillation column 84, all of the condensed product may be distilled off from the line 73b without refluxing. The non-condensable gas that has not been condensed by the condenser 84a may be merged into the line 62 through a line 73a and circulated to the absorption column 82, or may be discarded. Alternatively, the gas may be recycled just before the condenser configured to condense the overhead stream from the top of a distillation column such as a low-boiling component-removing column, a dehydration column, or a high-boiling component-removing column. The recycled non-condensable gas may then be circulated again from the line 62 to the absorption column 82 after the condensed component has been removed by the condenser.

The overhead stream (line 73) rich in useful components (particularly methyl iodide) from the top of the distillation column 84 may be recycled to the reactor, the evaporator, and a distillation column located downstream of the evaporator. Recycling to the reactor enables the reuse of useful components (particularly methyl iodide) in the reaction step, whereby improving economical aspects of production. When the offgas subjected to the absorption step is the exhaust gas from the decanter, the overhead stream rich in the useful components may contain a large amount of acetaldehyde because the low boiling component is concentrated more than the absorbent. Therefore, the overhead stream rich in the above useful components may be supplied to the acetaldehyde separation and removal system, or may be recycled to the reactor through a decanter after removing acetaldehyde with the acetaldehyde separation and removal system. On the other hand, a portion of the bottoms stream (line 74) from the bottom of the distillation column 84 is, continuously or in batches, discharged out of the system through a line 75, and a new portion of the absorbent is, continuously or in batches, supplied through a line 76, circulated through the absorption columns 81 and 82 through a line 68b, and reused as an absorbent in the absorption step. The bottoms stream (line 74) may be discharged out of the system without circulation, and a new absorbent may be supplied to the absorption columns 81 and 82. At least a portion of the bottoms stream (line 74) (for example, the solution discharged out of the system through the line 75) may be recycled to a reactor, an evaporator, a distillation column downstream of the evaporator (for example, the low-boiling component-removing column, the dehydration column, or the high-boiling component-removing column).

When a plate column is adopted as the distillation column 84, the theoretical number of plates is, for example, from 1 to 50, although it depends on the composition of the solution to be subjected to distillation. The reflux ratio is, for example, 3000 or less (for example, from 0 to 3000) depending on the theoretical number of plates. Inside the distillation column 84, the column top pressure is set to, for example, from 1 to 500 kPaG, and the column bottom pressure is set to be higher than the column top pressure, for example, from 10 to 700 kPaG. Inside the distillation column 84, the column top temperature is set to, for example, from 30 to 130° C., which is lower than the boiling point of the absorbent at the set column top pressure, and the column bottom temperature is set to, for example, a temperature equal to or higher than the boiling point of the absorbent at the set column bottom pressure and from 50 to 200° C. (preferably from 60 to 180° C.).

Figure 2:
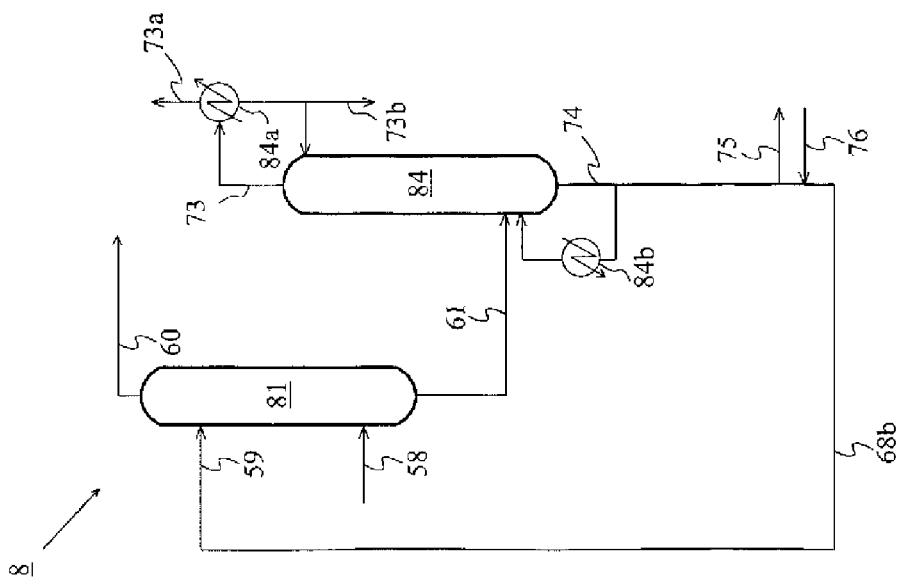
FIG. 2 is a schematic flow chart illustrating another example of a scrubber system.

FIG. 2 is an example of a schematic flow chart illustrating another embodiment of the scrubber system having the absorption step according to an embodiment of the present invention. In this example, the absorption step is performed only in the absorption column 81, and the gas component from the top of the absorption column 81 is discarded through the line 60, or used as a CO source to be introduced into the bottom of an evaporator 2 or the residual liquid stream recycling lines 18 and 19 described later. On the other hand, the solution (line 61) from the bottom of the absorption column 81 is supplied to the distillation column 84. Other parts are the same as the example of FIG. 1.

The method for producing acetic acid according to an embodiment of the present invention may include:
- a first absorption step of supplying at least a portion of offgas formed in the process to an absorption column and bringing the portion of the offgas into contact with a first absorbent to allow the first absorbent to absorb an iodine compound in the offgas, and separating into:
- a first gas component having a lower iodine compound concentration than the offgas; and
- a first solution containing the first absorbent and the iodine compound; and
- a second absorption step of, in an absorption column, bringing the first gas component into contact with a second absorbent to allow the second absorbent to absorb an iodine compound in the first gas component, the second absorbent having a composition different from that of the first absorbent, and separating into:
- a second gas component having a lower iodine compound concentration than the first gas component; and
- a second solution containing the second absorbent and an iodine compound. In this case, the absorption step according to an embodiment of the present invention is included in at least one of the first and second absorption steps.

When the method includes the first and second absorption steps, at least a portion of all the offgases generated in the acetic acid production process is supplied to the absorption column and subjected to the first and second absorption steps. Examples of the offgases subjected to the first and second absorption steps include the exhaust gas from the reactor in the reaction step, the exhaust gas from the evaporator in the evaporation step, the exhaust gas from the distillation column in the separation step, and the separation and the exhaust gas from the distillation column in the acetaldehyde separation and removal system described later.

The first and second absorption steps may be performed in one absorption column or two or more absorption columns, respectively. For example, when offgases from two or more processes are subjected to the first absorption step, the compositions and pressures of the offgases are different, so the first absorption step may be performed by the adsorption method using two or more absorption columns (for example, a high-pressure absorption column and a low-pressure absorption column). The first and second absorption steps may be performed in a single absorption column.

The second absorbent is an absorbent having a composition different from that of the first absorbent. Examples of such cases include a case where one of the absorbents includes a component which is not included in the other absorbent, and a case where even though the first and second absorbents include the same component, the proportion of at least one component is different. The absorption step is performed in two steps using two types of absorbents, and because the first and second absorbents have different compositions, the two types of absorbents have different solubility for hydrogen iodide and methyl iodide. Thus, the absorption step using one of the absorbents produces a solution enriched with one of hydrogen iodide and methyl iodide, while the absorption step using the other absorbent produces a solution enriched with the other one of hydrogen iodide and methyl iodide than the solution above, whereby separating and recovering hydrogen iodide and methyl iodide efficiently.

The first absorption step is the step of bringing an offgas formed in the process into contact (in particular, countercurrent contact) with the first absorbent to allow the first absorbent to absorb an iodine compound from the offgas and whereby separating the offgas into a first gas component and a first solution, where the first gas component has a lower iodine compound concentration than the offgas, and the first solution contains the first absorbent and the iodine compound. Specifically, the offgas is continuously introduced into an absorption column with which the first absorption step is performed; whereas the first absorbent is continuously introduced into the absorption column through a line provided at a higher position in the absorption column than a position at which the offgas is supplied. In the column, the offgas traveling upward and the first absorbent traveling downward are brought into countercurrent contact with each other to allow the first absorbent to absorb an iodine compound from the offgas. Then, the first gas component having a lower iodine compound concentration than the offgas is separated from a first solution containing the iodine compound and the first absorbent. The first absorption step may be performed in one absorption column or two or more absorption columns.

The second absorption step is the step of bringing the first gas component whose iodine compound concentration has been reduced in the first absorption step into contact with the second absorbent (particularly countercurrent contact), and separating the second gas component having a lower iodine compound concentration than the first gas component from the second solution containing the second absorbent and the iodine compound. Specifically, in the absorption column where the second absorption step is performed, the second absorbent is continuously introduced into the absorption column through a line provided at a higher position in the absorption column than a position at which the first gas component is supplied. In the column, the first gas component traveling upward and the second absorbent traveling downward are brought into countercurrent contact with each other to allow the second absorbent to absorb the iodine compound in the first gas component. Then, the second gas component having an iodine compound concentration lower than that of the first gas component is separated from the second solution containing the iodine compound and the second absorbent. The second absorption step may be performed in one absorption column or two or more absorption columns. When the first absorption step is performed using two or more absorption columns, the first gas components from the two or more absorption columns may be merged and subjected to the second absorption step, or the first gas components from the two or more absorption columns may be supplied to one absorption column or each supplied to two or more absorption columns, and subjected to the second absorption step. The first and second absorption steps may be performed in a single absorption column or in two or more different absorption columns.

The iodine compound to be absorbed by the absorbent in the first and second absorption steps is the same as that exemplified as the iodine compound to be absorbed in the absorption step according to an embodiment of the present invention described above. Among these, hydrogen iodide and methyl iodide are preferable. In particular, it is preferable that the iodine compound absorbed in the first absorption step is hydrogen iodide and the iodine compound absorbed in the second absorption step is methyl iodide. In the case where the first and second absorption steps are performed using different absorption columns, when hydrogen iodide is sufficiently absorbed in the first absorption step, the concentration of hydrogen iodide in the first gas component becomes extremely low, corrosion inside the absorption column where the second absorption step is performed is unlikely to occur. Thus, a material having low corrosion resistance (low-grade material) can be used for the absorption column. Further, when the concentration of hydrogen iodide in the first gas component supplied to the second absorption step is extremely reduced, there is little hydrogen iodide left to be absorbed by the second absorbent in the second absorption step. Therefore, the concentration of hydrogen iodide in the obtained second solution is also low, and corrosion inside the distillation column is less likely to occur when the second solution is distilled in the stripping step described later. Thus, a low-grade material can be used for the distillation column. Only one kind of the iodine compound or two or more kinds of the iodine compounds may be absorbed in the first and second absorption steps.

Therefore, it is preferable that at least one of the first absorbent and the second absorbent contains one or more liquids selected from the group consisting of a hydrocarbon, an ester of a carboxylic acid having 3 or more carbon atoms, an ester of a carboxylic acid and an alcohol having 2 or more carbon atoms, and an ether, and the other one of the first absorbent and the second absorbent contains water or an alkaline aqueous solution. That is, it is preferable that at least one of the first absorption step and the second absorption step is the absorption step according to an embodiment of the present invention, and the other one of the first absorption step and the second absorption step is an absorption step using an absorbent containing water or an alkaline aqueous solution. When water is used as the first or second absorbent, hydrogen iodide is highly soluble in water. When an alkaline aqueous solution is used, hydrogen iodide is not only highly soluble in water but also neutralized, whereby hydrogen iodide can be sufficiently absorbed.

In particular, the first absorbent preferably contains water or an alkaline aqueous solution from the viewpoint of high absorption of hydrogen iodide. The second absorbent preferably contains one or more liquids selected from the group consisting of a hydrocarbon, an ester of a carboxylic acid having 3 or more carbon atoms, an ester of a carboxylic acid and an alcohol having 2 or more carbon atoms, and an ether from the viewpoint of high absorption of methyl iodide. In this case, in the first absorption step, hydrogen iodide can be sufficiently recovered from offgas by the first absorbent, and methyl iodide is hardly absorbed by the first absorbent. And methyl iodide can be sufficiently recovered by the second absorbent in the second absorption step, whereby hydrogen iodide and methyl iodide can be efficiently separated and recovered. When such first and second absorbents are used, hydrogen iodide can be selectively recovered and removed in the first absorption step and methyl iodide can be selectively recovered and removed in the second absorption step.

Thus, methyl iodide containing almost no unnecessary hydrogen iodide can be recovered and can be easily reused in the reactor.

In a case where the gas component after hydrogen iodide is sufficiently absorbed in the first absorption step is treated in the second absorption step in the absorption step according to an embodiment of the present invention, and the second solution obtained in the second absorption step is distilled in the stripping step, the solvent having a low hydrogen iodide concentration and low polarity is distilled in the stripping step. Due to the synergistic effect of adopting the first and second absorption steps and providing the absorption step according to an embodiment of the present invention, corrosion in the distillation column in which the stripping step is performed can be further suppressed, and a SUS material can be used as the material of the distillation column. Further, when a hydrocarbon having from 5 to 7 carbon atoms is used as the absorbent in the absorption step according to an embodiment of the present invention, the boiling point of the absorbent is lowered, and corrosion in the distillation column can be further suppressed.

The preferred concentration of the liquid in an absorbent using one or more liquids selected from the group consisting of a hydrocarbon, an ester of a carboxylic acid having 3 or more carbon atoms, an ester of a carboxylic acid and an alcohol having 2 or more carbon atoms, and an ether is the same as the concentration in the absorbent used in the absorption step according to an embodiment of the present invention described above.

The water concentration in the absorbent using water is, for example, 10 ppm by mass or greater, preferably 20 ppm by mass or greater, more preferably 50 ppm by mass or greater, further preferably 100 ppm by mass or greater, and particularly preferably 200 ppm by mass or greater, and may be 300 ppm by mass or greater, 400 ppm by mass or greater, 500 ppm by mass or greater, 1000 ppm by mass or greater, 1 mass % or greater, 5 mass % or greater, 10 mass % or greater, 20 mass % or greater, 30 mass % or greater, 40 mass % or greater, 50 mass % or greater, 60 mass % or greater, 70 mass % or greater, 80 mass % or greater, and 90 mass % or greater. The upper limit of the above concentration is 100 mass %, and may be 99.999 mass %, 99.99 mass %, 99.9 mass %, 99.5 mass %, 99 mass %, or 98 mass %.

The hydrogen iodide concentration in the first solution determined by the subtraction method is, for example, 0.01 ppm by mass or more, and may be 0.1 ppm by mass or greater, 1 ppm by mass or greater, 10 ppm by mass or greater, 50 ppm by mass or greater, 100 ppm by mass or greater, 200 ppm by mass or greater, 300 ppm by mass or greater, 400 ppm by mass or greater, 500 ppm by mass or greater, 600 ppm by mass or greater, 700 ppm by mass or greater, 800 ppm by mass or greater, 900 ppm by mass or greater, 1000 ppm by mass or greater, 2000 ppm by mass or greater, 3000 ppm by mass or greater, 4000 ppm by mass or greater, 5000 ppm by mass or greater, 6000 ppm by mass or greater, 7000 ppm by mass or greater, 8000 ppm by mass or greater, 9000 ppm by mass or greater, and 1 mass % or greater. The hydrogen iodide concentration is, for example, 10 mass % or less, and may be 5 mass % or less, 3 mass % or less, 2 mass % or less, 1 mass % or less, 5000 ppm by mass or less, and 3000 ppm by mass or less.

The hydrogen iodide concentration in the first solution determined by the potentiometric titration method is, for example, 0.01 ppm by mass or greater, and may be 0.1 ppm by mass or greater, 1 ppm by mass or greater, 10 ppm by mass or greater, 50 ppm by mass or greater, 100 ppm by mass or greater, 200 ppm by mass or greater, 300 ppm by mass or greater, 400 ppm by mass or greater, 500 ppm by mass or greater, 600 ppm by mass or greater, 700 ppm by mass or greater, 800 ppm by mass or greater, 900 ppm by mass or greater, 1000 ppm by mass or greater, 2000 ppm by mass or greater, 3000 ppm by mass or greater, 4000 ppm by mass or greater, 5000 ppm by mass or greater, 6000 ppm by mass or greater, 7000 ppm by mass or greater, 8000 ppm by mass or greater, 9000 ppm by mass or greater, and 1 mass % or greater. The hydrogen iodide concentration is, for example, 5 mass % or less, and preferably 2 mass % or less. The hydrogen iodide concentration is, for example, 10 mass % or less, and may be 5 mass % or less, 3 mass % or less, 2 mass % or less, 1 mass % or less, 5000 ppm by mass or less, and 3000 ppm by mass or less.

The methyl iodide concentration in the first solution is, for example, 30 mass % or less, and may be 25 mass % or less, 20 mass % or less, 15 mass % or less, 10 mass % or less, 7 mass % or less, 5 mass % or less, 4 mass % or less, 3 mass % or less, 2 mass % or less, 1 mass % or less, 5000 ppm by mass or less, 2000 ppm by mass or less, and 1000 ppm by mass or less. The methyl iodide concentration is, for example, 10 ppm by mass or greater (for example, 50 ppm by mass or greater), preferably 100 ppm by mass or greater (for example, 500 ppm by mass or greater), and more preferably 1000 ppm by mass or greater (for example, 2000 ppm by mass or greater).

When a plurality of first absorption steps is provided, the concentration of each of the above components in the first solution is the concentration of each of the above components in all the first solutions separated and obtained in the plurality of first absorption steps.

The hydrogen iodide concentration in the second solution determined by the subtraction method is preferably lower than the hydrogen iodide concentration in the first solution, for example, 5 mass % or less, and may be 4 mass % or less, 3 mass % or less, 2 mass % or less, 1 mass % or less, less than 1 mass %, 5000 ppm by mass or less, 3000 ppm by mass or less, 2000 ppm by mass or less, 1000 ppm by mass or less, 700 ppm by mass or less, 500 ppm by mass or less, 300 ppm by mass or less, 200 ppm by mass or less, 100 ppm by mass or less, less than 100 ppm by mass, 50 ppm by mass or less, 30 ppm by mass or less, 20 ppm by mass or less, 10 ppm by mass or less, 5 ppm by mass or less, 3 ppm by mass or less, 2 ppm by mass or less, and 1 ppm by mass or less. The hydrogen iodide concentration is, for example, 0.0001 ppm by mass or greater, and may be 0.001 ppm by mass or greater, 0.01 ppm by mass or greater, 0.1 ppm by mass or greater, 0.5 ppm by mass or greater.

The hydrogen iodide concentration in the second solution determined by the potentiometric titration method is preferably lower than the hydrogen iodide concentration in the first solution, for example, 5 mass % or less, and may be 4 mass % or less, 3 mass % or less, 2 mass % or less, 1 mass % or less, less than 1 mass %, 5000 ppm by mass or less, 3000 ppm by mass or less, 2000 ppm by mass or less, 1000 ppm by mass or less, 700 ppm by mass or less, 500 ppm by mass or less, 300 ppm by mass or less, 200 ppm by mass or less, 100 ppm by mass or less, less than 100 ppm by mass, 50 ppm by mass or less, 30 ppm by mass or less, 20 ppm by mass or less, 10 ppm by mass or less, 5 ppm by mass or less, 3 ppm by mass or less, 2 ppm by mass or less, and 1 ppm by mass or less. The hydrogen iodide concentration is, for example, 0.0001 ppm by mass or greater, and may be 0.001 ppm by mass or greater, 0.01 ppm by mass or greater, 0.1 ppm by mass or greater, 0.5 ppm by mass or greater.

The methyl iodide concentration in the second solution is preferably higher than the methyl iodide concentration in the first solution, for example, is 1 ppm by mass or greater, and may be 1 ppm by mass or greater, 10 ppm by mass or greater, 50 ppm by mass or greater, 100 ppm by mass or greater, 1000 ppm by mass or greater, 5000 ppm by mass or greater, and 1 mass % or greater. The methyl iodide concentration is, for example, 20 mass % or less (for example, 15 mass % or less), preferably 10 mass % or less (for example, 8 mass % or less).

When a plurality of second absorption steps is provided, the concentration of each of the above components in the second solution is the concentration of each of the above components in all the second solutions separated and obtained in the plurality of second absorption steps.

When the first and second absorption steps are provided, a distillation step (stripping step) of subjecting the first solution obtained in the first absorption step and/or the second solution obtained in the second absorption step to distillation may be provided. In the stripping step, the first and/or second solution is subjected to distillation to be separated into an overhead stream richer in a low boiling component than the first and/or second absorbent and a bottoms stream rich in the first and/or second absorbent. When the method of producing acetic acid includes the stripping step, the useful components can be separated from the bottoms stream rich in the first and/or second absorbents, and the useful components can be recycled to the reactor, the evaporator, the distillation column, and the like, and the separated absorbent can be reused as the absorbent in the first and/or second absorption steps; whereby improving economical aspects of the production.

At least a portion of the bottoms stream from the bottom of the distillation column, which is separated and acquired in the stripping step, may be continuously discharged out of the system, and at least a portion may be circulated to the first and/or second absorption column. Further, at least a portion of the bottoms stream may be recycled to the reactor, the evaporator, the purification step (distillation step) downstream of the evaporator, or the like. Other preferred embodiments of the stripping step are as described above.

Figure 3:
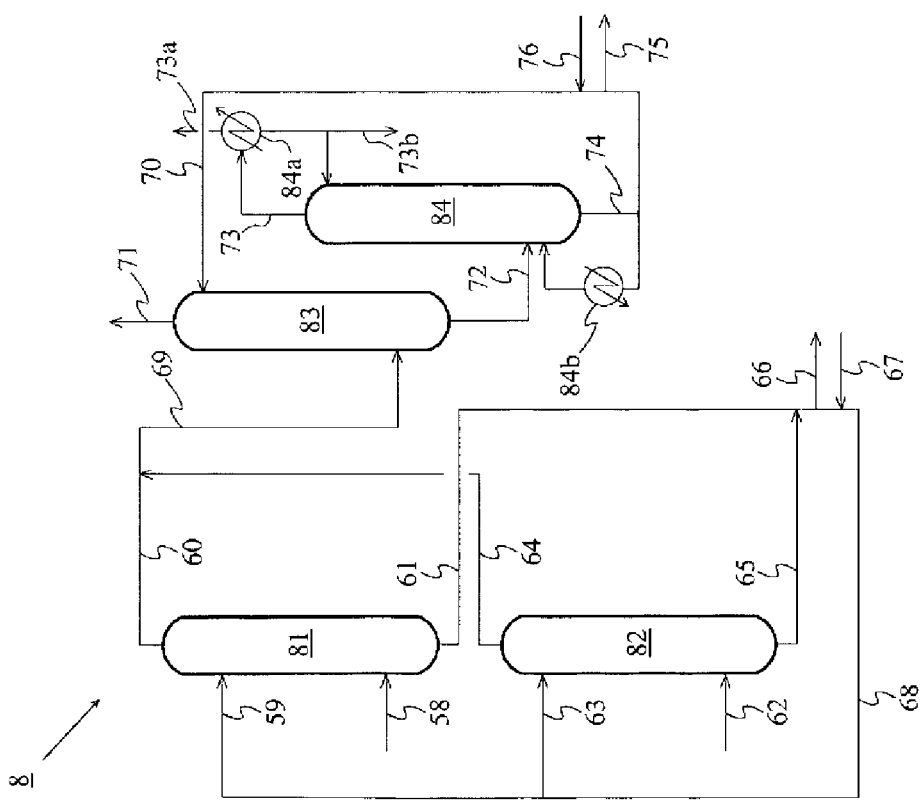
FIG. 3 is a schematic flow chart illustrating still another example of a scrubber system.

FIG. 3 is an example of a schematic flow chart illustrating an embodiment of a scrubber system including the first and second absorption steps in the present invention. The scrubber system 8 includes an absorption column 81, an absorption column 82, an absorption column 83, and a distillation column 84. In the method for producing acetic acid of the present embodiment, the first absorption step is performed in each of the absorption columns 81 and 82, a second absorption step is performed in the absorption column 83, and a stripping step is performed in the distillation column 84, respectively.

In the scrubber system 8 illustrated in FIG. 3, the absorption step according to an embodiment of the present invention is performed in at least one of the absorption columns 81 to 83. It is preferable that at least one of the first absorption step and the second absorption step is the absorption step according to an embodiment of the present invention. When the first absorption step is the absorption step according to an embodiment of the present invention, it is preferable that the absorption steps in both the absorption columns 81 and 82 are the absorption step according to an embodiment of the present invention. The absorbents used in the absorption columns 81 and 82 may be the same or different.

The absorption column 81 is a unit (high-pressure absorption column) configured to perform the first absorption step of absorbing and recovering the iodine compound from the high-pressure gas of the offgas. The first absorption step is a step of bringing the high-pressure gas into contact with the first absorbent to allow the first absorbent to absorb the iodine compound in the high-pressure gas, and separating the first gas component having a lower iodine compound concentration than the high-pressure gas from the first solution containing the first absorbent and the iodine compound.

Specifically, the high-pressure gas is continuously introduced into the absorption column 81 through a line 58 (high-pressure gas supply line), while the first absorbent is continuously introduced into the absorption column 81 through a line 59 (first absorbent supply line) located at a position higher than a position where the high-pressure gas is introduced. Thus, the high-pressure gas traveling upward and the first absorbent traveling downward in the column are brought into countercurrent contact, and the iodine compound in the high-pressure gas is absorbed by the first absorbent. Then, the first gas component having a lower iodine compound concentration than the high-pressure gas and the first solution containing the iodine compound and the first absorbent are separated, and the first gas component is obtained from the top of the absorption column 81 through the line 60, and the first solution is obtained from the bottom of the absorption column 81 through the line 61.

The high-pressure gas is, for example, an exhaust gas from the reactor (or reaction step). The exhaust gas discharged from the reactor may be directly supplied to the absorption column 81 through the line 58. Alternatively, the condensed component of the exhaust gas discharged from the reactor may be separated by a condenser, and the resultant non-condensable gas may be supplied to the absorption column 81 through the line 58. The temperature of the first absorbent before being supplied to the absorption column 81 is, for example, from 1 to 120° C., which is a temperature within a range in which the first absorbent does not freeze and does not boil.

The absorption column 81 includes a rectification column such as a plate column and a packed column. The packing in the packed column may be either a structured packing or a random packing. When a plate column is adopted, the theoretical number of plates is, for example, from 1 to 100. The pressure in the column is, for example, atmospheric pressure to 5 MPaG, which is usually equal to or lower than the pressure in the reactor. The temperature inside the column is, for example, about 1 to 120° C.

The absorption column 82 is a unit configured to perform the first absorption step of absorbing and recovering an iodine compound from the low-pressure gas of the offgases (low-pressure absorption column). The first absorption step is a step of bringing the low-pressure gas into contact with the first absorbent to allow the first absorbent to absorb the iodine compound in the low-pressure gas, and separating the first gas component having a lower iodine compound concentration than the low-pressure gas from the first solution containing the first absorbent and the iodine compound.

Specifically, the low-pressure gas is continuously introduced into the absorption column 82 through a line 62 (low-pressure gas supply line), while the first absorbent is continuously introduced into the absorption column 82 through a line 63 (first absorbent supply line) located at a position higher than a position where the low-pressure gas is introduced. Thus, the low-pressure gas traveling upward and the first absorbent traveling downward in the column are brought into countercurrent contact, and the iodine compound in the low-pressure gas is absorbed by the first absorbent. Then, the first gas component having a lower iodine compound concentration than the low-pressure gas and the first solution containing the iodine compound and the first absorbent are separated, and the first gas component is obtained from the top of the absorption column 82 through a line 64, and the first solution is obtained from the bottom of the absorption column 82 through a line 65.

Examples of the low-pressure gas include an exhaust gas from the evaporator (or evaporation step), an exhaust gas from the low-boiling component-removing column (or low-boiling component-removing step), an exhaust gas from the decanter configured to store the condensed liquid resulting from condensing the overhead stream rich in a low boiling component from the low-boiling component-removing column, an exhaust gas from the dehydration column (or dehydration step), and exhaust gas from the high-boiling component-removing column (or high-boiling component-removing step). These exhaust gases may be directly supplied to the absorption column 82 through the line 62. Alternatively, the condensed component may be separated by a condenser, and the resultant non-condensable gas may be supplied to the absorption column 82 through the line 62. The temperature of the first absorbent before being supplied to the absorption column 82 is the same as the temperature of the first absorbent before being supplied to the absorption column 81.

The absorption column 82 includes a rectification column such as a plate column and a packed column. The packing in the packed column may be either a structured packing or a random packing. When a plate column is adopted, the theoretical number of plates is, for example, from 1 to 100. The pressure in the column is, for example, atmospheric pressure to 5 MPaG, which is usually equal to or lower than the pressure in the reactor. The temperature inside the column is, for example, about 1 to 120° C.

The first gas component (line 60) from the top of the absorption column 81 and the first gas component (line 64) from the top of the absorption column 82 are merged and supplied, through the line 69, to the absorption column 83 where the second absorption step is performed. On the other hand, the first solution from the bottom of the absorption column 81 (line 61) and the first solution from the bottom of the absorption column 82 (line 65) are merged and a portion of them is, continuously or in batches, discharged out of the system through line 66. A new portion of the first absorbent is, continuously or in batches, supplied through the line 67, the stream goes through the line 68 then is divided into the lines 59 and 63 and circulated into the absorption columns 81 and 82, respectively. Thus, the first solution is reused as the first absorbent in the first absorption step. The first solution may be completely discharged from the system without circulation, and a new portion of the first absorbent may be supplied to the absorption columns 81 and 82. At least a portion of the first solution (for example, the first solution discharged from the system through the line 66) may be recycled to a reactor, an evaporator, or a distillation column configured to perform a distillation step. For example, when the first absorbent contains water, the first absorbent efficiently absorbs hydrogen iodide, and most of the first solution is circulated to the first absorption column and reused as the first absorbent, and when hydrogen iodide is concentrated, a portion of it is recycled to the reactor. This is because water is consumed by a shift reaction with carbon monoxide ($H_2O + CO \rightarrow H_2 + CO_2$) in the reactor. When the first solution contains a large amount of water, water may not be sufficiently consumed in the reactor. Therefore, instead of recycling to the reactor or in combination with recycling to the reactor, the first solution may be recycled to the aqueous phase in the decanter, the dehydration column, and the high-boiling component-removing column. In this case, for example, the component in the first solution is concentrated in the aqueous phase in the decanter, at the top of the dehydration column, and at the top of the high-boiling component-removing column. The portion of the resulting material is recycled to the reactor, and the other portion is discharged out of the system. FIG. 3 illustrates an example in which the same first absorbent is used in the absorption columns 81 and 82, but different first absorbents may be used and each of the first absorbents is circulated, discharged from the system, recycled, or the like.

The absorption column 83 is a unit (usually a low-pressure absorption column) configured to perform the second absorption step of absorbing and recovering an iodine compound from the first gas component discharged from the first absorption step. The second absorption step is a step of bringing the first gas component into contact with the second absorbent to allow the second absorbent to absorb the iodine compound in the first gas component, and separating the second gas component having a lower iodine compound concentration than the first gas component from the second solution containing the second absorbent and the iodine compound.

Specifically, the first gas component is continuously introduced into the absorption column 83 through the line 69, while the second absorbent is continuously introduced into the absorption column 83 through the line 70 (second absorbent supply line) located at a position higher than a position where the first gas component is introduced. Thus, the first gas component traveling upward and the second absorbent traveling downward are brought into countercurrent contact, and the iodine compound in the first gas component is absorbed by the second absorbent. Then, the second gas component having a lower iodine compound concentration than the first gas component and the second solution containing the iodine compound and the second absorbent are separated, the second gas component is obtained from the top of the absorption column 83 through the line 71, and the second solution is obtained from the bottom of the absorption column 83 through the line 72. The temperature of the second absorbent before being supplied to the absorption column 83 is, for example, from 1 to 120° C. In this temperature range, the second absorbent does not freeze and does not boil.

The second gas component (line 71) from the top of the absorption column 83 is a gas from which useful components have been collected and removed and is discarded. The gas discharged from the line 71 may be used as a CO source to be introduced into the bottom of the evaporator 2 or the residual liquid stream recycling lines 18 and 19 described later. On the other hand, the second solution (line 72) from the bottom of the absorption column 83 is supplied to a distillation column 84.

The absorption column 83 includes a rectification column such as a plate column and a packed column. The packing in the packed column may be either a structured packing or a random packing. When a plate column is adopted, the theoretical number of plates is, for example, from 1 to 100. The pressure in the column is, for example, atmospheric pressure to 5 MPaG, which is usually equal to or lower than the pressure in the reactor. The temperature inside the column is, for example, about 1 to 120° C.

The distillation column 84 is a unit configured to perform a stripping step. The stripping step according to an embodiment of the present embodiment is a step of subjecting the second solution to distillation, and separating the second solution into an overhead stream rich in useful components (particularly methyl iodide) and a bottoms stream rich in the second absorbent. From the top of the distillation column 84, vapor, which is an overhead stream, is continuously drawn into a line 73. From the bottom of the distillation column 84, a bottoms liquid is continuously drawn into the line 74. 84*b* indicates a reboiler.

More specifically, the second solution continuously introduced into the distillation column 84 is distilled to be separated into an overhead stream rich in useful components (particularly methyl iodide) and a bottoms liquid rich in the second absorbent. The distillation column 84 includes, for example, a rectification column such as a plate column and a packed column. The overhead stream of the distillation column 84 is introduced into a condenser 84*a* through the line 73. The condenser 84*a* cools and partially condenses the overhead stream from the distillation column 84 to separate the overhead stream into the condensed component and the gas component. A portion of the condensed component is refluxed to the distillation column 84, and the other portion is distilled from a line 73*b*. Although FIG. 3 illustrates an example in which the condensed component is refluxed to the distillation column 84, all of the condensed product may be distilled off from the line 73*b* without refluxing. The non-condensable gas that has not been condensed by the condenser 84*a* may be merged into the line 62 through a line 73*a* and circulated to the absorption column 82, or may be discarded. Alternatively, the gas may be recycled just before the condenser configured to condense the overhead stream from the top of a distillation column such as a low-boiling component-removing column, a dehydration column, or a high-boiling component-removing column. The recycled non-condensable gas may then be circulated again from the line 62 to the absorption column 82 after the condensed component has been removed by the condenser.

The overhead stream (line 73) rich in useful components (particularly methyl iodide) from the top of the distillation column 84 may be recycled to a reactor, an evaporator, a distillation column downstream of the evaporator, or the like. Recycling to the reactor enables the reuse of useful components (particularly methyl iodide) in the reaction step, whereby improving economical aspects of production. When the offgas subjected to the first absorption step is the exhaust gas from the decanter, the overhead stream rich in the useful components may contain a large amount of acetaldehyde because the low boiling component is concentrated more than the second absorbent. Therefore, the overhead stream rich in the above useful components may be supplied to the acetaldehyde separation and removal system, or may be recycled to the reactor through a decanter after removing acetaldehyde with the acetaldehyde separation and removal system. On the other hand, a portion of the bottoms stream (line 74) from the bottom of the distillation column 84 is, continuously or in batches, discharged out of the system through a line 75, and a new portion of the second absorbent is, continuously or in batches, supplied through a line 76, circulated through the absorption columns 83 through a line 70, and reused as the second absorbent in the second absorption step. The second solution may be completely discharged from the system without circulation, and a new portion of the second absorbent may be supplied to the absorption column 83. Furthermore, at least a portion of the second solution (for example, the second solution discharged from the system through the line 75) may be recycled to a reactor, an evaporator, a low-boiling component-removing column, a dehydration column, and a high-boiling component-removing column.

The preferable conditions of the distillation column when the plate column is adopted as the distillation column 84 are the same as the conditions of the distillation column 84 illustrated in FIG. 1.

Figure 4:
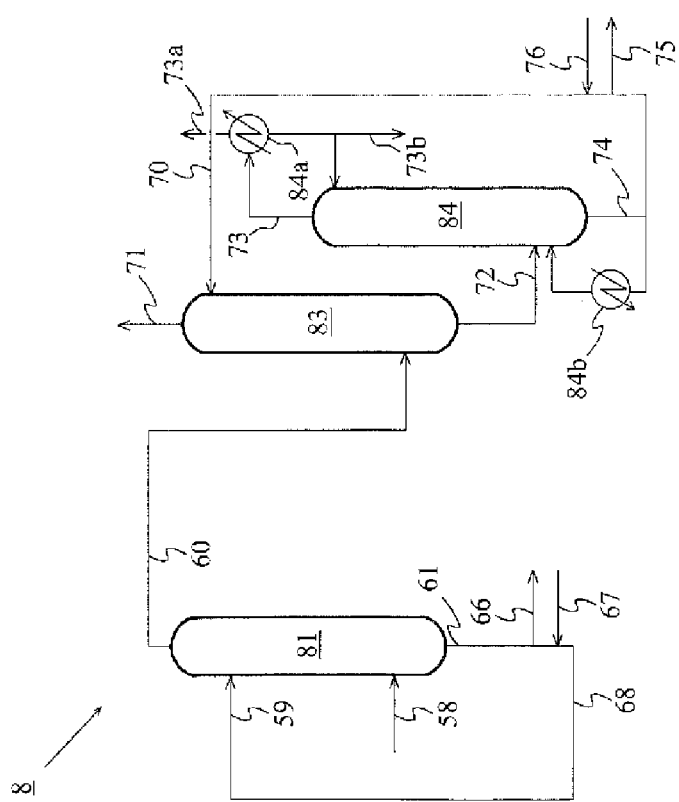
FIG. 4 is a schematic flow chart illustrating still another example of a scrubber system.

FIG. 4 is an example of a schematic flow chart illustrating another embodiment of the scrubber system having the first and second absorption steps. In this example, the first absorption step is performed only in the absorption column 81, the first gas component from the top of the absorption column 81 is supplied through the line 60 to the absorption column 83 in which the second absorption step is performed, the first solution is drawn from the bottom of the column through line 61, a portion of the first solution is discharged out of the system (line 66), a new portion of the first absorbent is supplied to the first solution (line 67), and recirculated to the absorption column 81 through the line 59 and reused as the first absorbent. Other parts are the same as the example of FIG. 3.

Figure 5:
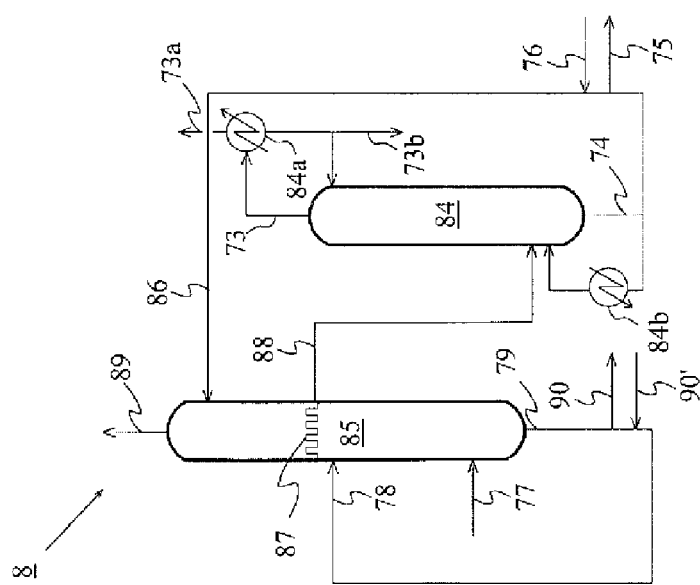
FIG. 5 is a schematic flow chart illustrating still another example of a scrubber system.

FIG. 5 is an example of a schematic flow chart illustrating still another embodiment of the scrubber system having the first and second absorption steps. In this example, the first and second absorption steps are performed in a single absorption column 85. Specifically, in the first absorption step, the offgas in the process is continuously introduced into the absorption column 85 through a line 77 (offgas supply line), while the first absorbent is continuously introduced into the absorption column 85 through a line 78 (first absorbent supply line) located at a position higher than a position where the offgas is introduced. Thus, the offgas traveling upward and the first absorbent traveling downward in the column are brought into countercurrent contact, and the iodine compound in the offgas is absorbed by the first absorbent. Then, the first gas component having a lower iodine compound concentration than the offgas is separated from the first solution containing the iodine compound and the first absorbent. The first gas component further travels upward in the absorption column 85, and the first solution is discharged from the bottom of the absorption column 85 through the line 79. In the second absorption step, the first gas component travels further upward in the absorption column 85 relative to the position at which the first absorbent is introduced, while the second absorbent is continuously introduced through a line 86 near the top of the absorption column 85. The first gas component traveling upward and the second absorbent traveling downward in the column are brought into countercurrent contact, and the iodine compound in the first gas component is absorbed by the second absorbent. Then, the first gas component is separated into the second gas component having a lower iodine compound concentration than the first gas component and the second solution containing the iodine compound and the second absorbent. The second gas component is drawn from the top of the absorption column 85 through the line 89, and the second solution is collected by a unit (such as a chimney tray) 87 that can receive the liquid traveling downward from the position where the second absorbent is introduced and thus the second solution is drawn from a line 88. The second solution from the absorption column 85 is supplied through the line 88 to the distillation column 84 where the stripping step is performed, the first solution is drawn from the bottom of the column through a line 79, and a portion thereof is discharged out of the system (line 90). A new portion of the first absorbent is supplied to the first solution (line 90'), circulated to the absorption column 85 as the first absorbent through the line 78, and the second solution is reused. In addition, a portion of the bottoms stream (line 74) from the bottom of the distillation column 84 is, continuously or in batches, discharged to the outside of the system through the line 75, and a new portion of the second absorbent is, continuously or in batches, supplied through the line 76, circulated to the absorption column 85 through the line 86, and reused as the second absorbent in the second absorption step. Other parts are the same as the example of FIG. 3. That is, the second solution from the absorption column 85 is supplied to the stripping step, but the first and/or second solution may be recycled to various parts of the process.

In the method for producing acetic acid according to an embodiment of the present invention, the acetic acid production process may include a carbonylation reaction step in which methanol is reacted with carbon monoxide to produce acetic acid, and a separation step in which, using one or more evaporators and/or distillation columns, the reaction mixture obtained in the carbonylation reaction step is separated into a stream containing a metal catalyst, an acetic acid stream rich in acetic acid, and a stream rich in a low boiling component than the acetic acid stream. The separation step preferably includes, for example, an evaporation step of separating the reaction mixture obtained in the above carbonylation reaction step into a vapor stream and a residual liquid stream in an evaporator, and a low-boiling component-removing step in which the vapor stream is subjected to distillation to be separated into an overhead stream rich in a low boiling component and a first acetic acid stream rich in acetic acid. The separation step may include a dehydration step in which the first acetic acid stream is distilled to be separated into a water-rich overhead stream and a second acetic acid stream that is richer in acetic acid than the first acetic acid stream.

The separation step may include, instead of the evaporation step and the low-boiling component-removing step, a step of separating the reaction mixture obtained in the carbonylation reaction step into a stream containing the catalyst, an overhead stream rich in a low boiling component, and a first acetic acid stream rich in acetic acid (evaporation low-boiling component-removing step). The separation step may include, instead of the low-boiling component-removing step and dehydration step, a low-boiling component-removing step (so-called low-boiling component-removing dehydration step) that also has a function of the dehydration step above, that is, a step of subjecting the vapor stream to distillation to separate the vapor into an overhead stream rich in a low boiling component and an acetic acid stream dehydrated to a water concentration equivalent to that of the second acetic acid stream. Therefore, the evaporation low-boiling component-removing step may be a step (evaporation low-boiling component-removing dehydration step) having the function of the dehydration step. The acetic acid-rich acetic acid stream obtained from the low-boiling component-removing dehydration step and the evaporation low-boiling component-removing dehydration step corresponds to the second acetic acid stream above.

The method for producing acetic acid according to an embodiment of the present invention may further include at least one of the following steps (a) to (c):
(a) a high-boiling component-removing step of distilling the first or second acetic acid stream and separating the acetic acid stream into a bottoms stream rich in high boiling components and a third acetic acid stream rich in acetic acid than the acetic acid stream before distillation;
(b) an adsorption removal step of treating the first, second or third acetic acid stream with an ion exchange resin to produce a fourth acetic acid stream; and
(c) a product step in which the first, second, third, or fourth acetic acid stream is distilled to produce a fifth acetic acid stream that is richer in acetic acid than the acetic acid stream before distilling.

The method for producing acetic acid according to an embodiment of the present invention may include an acetaldehyde separation and removal system that is configured to separate acetaldehyde from at least a portion of the condensed liquid produced by condensing the stream rich in a low boiling component, using one or more distillation columns.

In such a method for producing acetic acid according to an embodiment of the present invention, it is preferable that at least one of the offgases selected from the group consisting of the exhaust gas from the reactor, the exhaust gas from the evaporator, the exhaust gas from the distillation column in the separation step, and the exhaust gas from the distillation column in the acetaldehyde separation and removal system is supplied to the absorption column and subjected to the absorption step or the first absorption step according to an embodiment of the present invention.

In such a method for producing acetic acid according to an embodiment of the present invention, the overhead stream rich in methyl iodide separated and obtained in the stripping step may be recycled into the reaction step, the evaporation step, and/or the distillation step. This is because methyl iodide can be usefully reused in the reaction step in the reactor.

In addition, in the method for producing acetic acid according to an embodiment of the present invention, when an absorbent containing one or more liquids selected from the group consisting of a hydrocarbon, an ester of a carboxylic acid having 3 or more carbon atoms, an ester of a carboxylic acid and an alcohol having 2 or more carbon atoms, and an ether is used, the bottoms stream separated and obtained in the stripping step and rich in the liquid above may be recycled to the reaction step, the evaporation step, and/or the distillation step, or may be charged in an alkane removal column and subjected to distillation and removal. Alternatively, it may be discarded as it is outside the process system.

In the method for producing acetic acid according to an embodiment of the present invention, it is preferred that a solution, which contains water and is obtained in the absorption step when an absorbent containing water is used, is recycled to one or more devices selected from the group consisting of the reactor, the decanter configured to store the condensed liquid, the dehydration column, and the high-boiling component-removing column. This is because water is consumed by the shift reaction of carbon monoxide $(H_2+CO \rightarrow H_2+CO_2)$ in the reactor. When the water is recycled into the aqueous phase in the decanter, it is treated together with the aqueous phase. When the solution is recycled to the dehydration column, the water is concentrated on the top of the dehydration column, and when the solution is recycled to the high-boiling component-removing column, the water is concentrated on the top of the high-boiling component-removing column, and then recycled or discarded.

Figure 6:
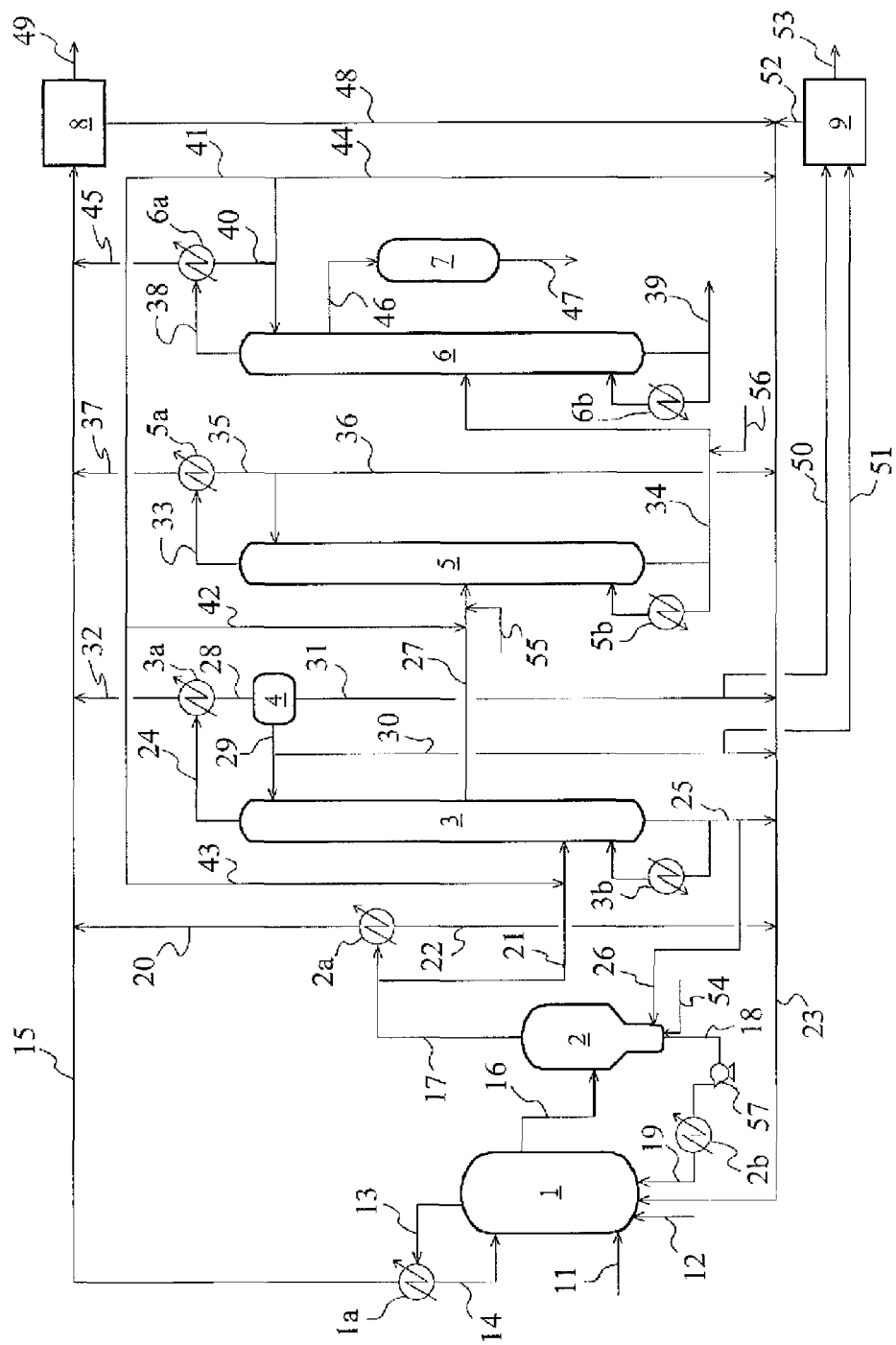
FIG. 6 is a production flow chart illustrating an embodiment of an acetic acid production system.

Hereinafter, an embodiment of the method for producing acetic acid of the present invention will be described. FIG. 6 is an example of a production schematic flow chart (methanol method carbonylation process) illustrating an embodiment of an acetic acid production system. An acetic acid production apparatus related to this acetic acid production schematic flow chart includes a reactor 1, an evaporator 2, a distillation column 3, a decanter 4, a distillation column 5, a distillation column 6, an ion exchange resin column 7, a scrubber system 8, an acetaldehyde separation and removal system 9, condensers 1a, 2a, 3a, 5a, 6a, a heat exchanger 2b, reboilers 3b, 5b, 6b, lines 11 to 56, and a pump 57, and is configured to produce acetic acid continuously.

In the method for producing acetic acid of the present embodiment, in the reactor 1, the evaporator 2, the distillation column 3, the distillation column 5, the distillation column 6, and the ion exchange resin column 7, a reaction step, an evaporation step (flash step), a first distillation step, a second distillation step, a third distillation step, and an adsorption removal step are performed, respectively. The first distillation step is also called a low-boiling component-removing step, the second distillation step is also called a dehydration step, and the third distillation step is also called a high-boiling component-removing step. In the present embodiment, the process is not limited to the above, and in particular, equipment of the distillation column 5, the distillation column (high-boiling component-removing column) 6, the ion exchange resin column 7, or the acetaldehyde separation and removal system 9 (acetaldehyde removal column, etc.) may not be provided. As will be described later, a product column may be provided downstream of the ion exchange resin column 7.

The reactor 1 is a unit configured to perform a reaction step. In this reaction step, acetic acid is continuously produced by the reaction represented by the following chemical formula (1) (carbonylation reaction of methanol). In the steady operation state of the acetic acid production apparatus, there is a reaction mixture that is agitated by, for example, a stirrer in the reactor 1. The reaction mixture contains methanol and carbon monoxide as raw materials, a metal catalyst, a co-catalyst, water, acetic acid which is the object of the production, and various by-products. The liquid phase and the gas phase are in equilibrium.

$$CH_3OH+CO \rightarrow CH_3COOH \qquad (1)$$

The raw materials in the reaction mixture are liquid methanol and gaseous carbon monoxide. Methanol is continuously supplied from the methanol reservoir (not shown) to the reactor 1 through the line 11 at a predetermined flow rate. Carbon monoxide is continuously supplied from the carbon monoxide reservoir (not shown) to the reactor 1 through the line 12 at a predetermined flow rate. Carbon monoxide does not necessarily have to be pure carbon monoxide, and may contain a small amount (for example, 5 mass % or less, preferably 1 mass % or less) of other gases such as nitrogen, hydrogen, carbon dioxide, and oxygen.

The metal catalyst in the reaction mixture is for accelerating the carbonylation reaction of methanol, and may be, for example, a rhodium catalyst or an iridium catalyst. The rhodium catalyst may be a rhodium complex represented by chemical formula $[Rh(CO)_2I_2]^-$. The iridium catalyst may be, for example, an iridium complex represented by chemical formula $[Ir(CO)_2I_2]^-$. The metal catalyst is preferably a metal complex catalyst. The concentration of the catalyst in the reaction mixture (in terms of metal) is, for example, from 200 to 10000 ppm by mass, preferably from 300 to 5000 ppm by mass, and more preferably from 400 to 2500 ppm by mass with respect to the entire liquid phase (reaction mixture) of the reaction mixture.

The co-catalyst is an iodide for assisting the action of the catalyst, and may be, for example, methyl iodide or ionic iodide. Methyl iodide can exhibit an action that promotes the catalytic action of the catalyst described above. The concentration of methyl iodide is, for example, from 1 to 20 mass %, preferably from 5 to 15 mass % with respect to the entire liquid phase of the reaction mixture. The ionic iodide is an iodide that produces iodide ions in the reaction solution (particularly an ionic metal iodide), and can exhibit the action of stabilizing the catalyst and the action of suppressing side reactions. Examples of the ionic iodide include alkali metal iodides such as lithium iodide, sodium iodide, and potassium iodide. The concentration of the ionic iodide in the reaction mixture is, for example, from 1 to 25 mass %, and preferably from 5 to 20 mass %, with respect to the entire liquid phase of the reaction mixture. For example, when an iridium catalyst or the like is used, a ruthenium compound or an osmium compound may also be used as a co-catalyst. The total amount of these compounds used is, for example, from 0.1 to 30 mol (in terms of metal), preferably from 0.5 to 15 mol (in terms of metal) with respect to 1 mol of iridium (in terms of metal).

The water in the reaction mixture is a component necessary for producing acetic acid in terms of the reaction mechanism of the carbonylation reaction of methanol, and is also a component necessary for solubilizing the water-soluble component of the reaction system. The concentration of water in the reaction mixture is, for example, from 0.1 to 15 mass %, preferably from 0.5 to 10 mass %, more preferably from 1 to 6 mass %, and even more preferably from 1.5 to 4 mass % based on the entire liquid phase of the reaction mixture. The water concentration is preferably 15 mass % or less in order to suppress the energy required for removing water in the acetic acid purification process and promote the efficiency of acetic acid production. In order to control the water concentration, water may be continuously supplied to the reactor 1 at a predetermined flow rate.

The acetic acid in the reaction mixture contains acetic acid prepared in advance in the reactor 1 before the operation of the acetic acid production apparatus, and acetic acid produced as a main product of the carbonylation reaction of methanol. Such acetic acid can function as a solvent in the reaction system. The concentration of acetic acid in the reaction mixture is, for example, from 50 to 90 mass %, and preferably from 60 to 80 mass %, based on the entire liquid phase of the reaction mixture.

Examples of the main by-product contained in the reaction mixture include methyl acetate. This methyl acetate can be produced by the reaction of acetic acid with methanol. The concentration of methyl acetate in the reaction mixture is, for example, from 0.1 to 30 mass %, preferably from 1 to 10 mass %, based on the entire liquid phase of the reaction mixture.

Examples of the by-product contained in the reaction mixture also include hydrogen iodide. This hydrogen iodide is inevitably generated due to the reaction mechanism of the carbonylation reaction of methanol when the catalyst or co-catalyst above is used. The concentration of hydrogen iodide in the reaction mixture is, for example, from 0.01 to 2 mass % with respect to the entire liquid phase of the reaction mixture.

Examples of the by-product include hydrogen, methane, carbon dioxide, acetaldehyde, crotonaldehyde, 2-ethylcrotonaldehyde, dimethyl ether, alkanes, formic acid, and propionic acid, and alkyl iodides such as hexyl iodide and decyl iodide. The reaction mixture may contain metals such as iron, nickel, chromium, manganese, and molybdenum (hereinafter may be referred to as "corrosive metals") generated by corrosion of the equipment, and other metals such as cobalt, zinc, and copper. The corrosive metal and other metals above may be collectively referred to as "corrosion metal or the like".

In the reactor 1 in which the above reaction mixture is present, the reaction temperature is set to, for example, from 150 to 250° C., and the reaction pressure is set to the total pressure is set to, for example, from 1.5 to 3.5 MPa (absolute pressure), and the partial pressure of carbon monoxide is set to, for example, from 0.4 to 1.8 MPa (absolute pressure), preferably from 0.6 to 1.6 MPa (absolute pressure), and more preferably from 0.9 to 1.4 MPa (absolute pressure).

The vapor in the gas phase in the reactor 1 during operation of the apparatus includes, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, formic acid, and propionic acid. This vapor can be drawn from the reactor 1 through the line 13. It is possible to control the pressure in the reactor 1 by adjusting the amount of vapor drawn. For example, the pressure in the reactor 1 is maintained constant. The vapor drawn from the reactor 1 is introduced into the condenser 1a.

The condenser 1a cools and partially condenses the vapor from the reactor 1 to separate the vapor into a condensed component and a gas component. The condensed component contains, for example, methyl iodide, hydrogen iodide, water, methyl acetate, acetic acid, dimethyl ether, methanol, acetaldehyde, formic acid, and propionic acid, and the condensed component is introduced from the condenser 1a into the reactor 1 through the line 14 and recycled. The gas component includes, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid, and the gas component is supplied from the condenser 1a to the scrubber system 8 through the line 15.

In FIG. 6, the gas component from a condenser 2a (line 20), the gas component from a condenser 3a (line 32), the gas component from a condenser 5a (line 37), and the gas components from a condenser 6a (line 45) are all merged into the line 15 and supplied to the scrubber system 8 (pattern A). Alternatively, only the gas component from the condenser 1a may be supplied to the scrubber system 8 through the line 15, and all the gas components from the condensers 3a, 5a, and 6a (lines 32, 37, and 45) are merged into the line 20 and supplied to the scrubber system 8 (pattern B). In the case of pattern A, for example, the gas component from the condenser 1a is supplied to the absorption column 81 or the absorption column 85 through the line 15 and the line 58 in the scrubber system 8 illustrated in FIG. 2 or 4 or the line 77 in the scrubber system 8 illustrated in FIG. 5. In the case of pattern B, for example, the gas component from the condenser 1a is supplied to the absorption column 81 through the line 15 and the line 58 in the scrubber system 8 illustrated in FIG. 1 or 3, and the gas component passing through the line 20 is supplied to the absorption column 82 through the line 62 in the scrubber system 8 illustrated in FIG. 1 or FIG. 3.

In the scrubber system 8, through the absorption step according to an embodiment of the present invention and, if necessary, further through the stripping step as described above, the useful components (for example, methyl iodide, methanol, dimethyl ether, water, methyl acetate, and acetic acid) are separated and recovered from the gas component (line 15) from the condenser 1a. For this separation and recovery, in the present embodiment, a wet method using an absorbing liquid that collects useful components in the gas component is employed. For example, a condensed component of vapor from the distillation column 6 described later can be used as the absorbing liquid. The separated and recovered useful components (for example, methyl iodide) are introduced into the reactor 1 from the scrubber system 8 (particularly, the line 73 from the top of the distillation column 84 in the stripping step) through the recycling line 48 and recycled. Although not illustrated, the line 48 may lead to the charging line of each of the condensers 1a, 2a, 3a, and 5a to cool, condense, and recover useful components. The gas after the collection of the useful components (for example, the line 69 in FIG. 1 and the line 60 in FIG. 2) is discarded as it is, or used as a CO source to be introduced into the bottom of the evaporator 2 or the residual liquid stream recycling lines 18 and 19. The gas after the collection of the useful components (for example, a line 71 in FIGS. 3 and 4) is discarded through the line 49. The gas after the collection of the useful components (for example, lines 73a and 89 in FIG. 5) may be separated from the condensed components by a condenser and/or recirculated to the absorption column. The gas discharged from the line 49 may be used as a CO source to be introduced into the bottom of the evaporator 2 or the residual liquid stream recycling lines 18 and 19 described later. The treatment in the scrubber system 8 and the subsequent recycling and disposal are the same for the gas components (lines 20, 32, 37, and 45) to be supplied to the scrubber system 8 from other condensers.

As described above, acetic acid is continuously produced in the reactor 1 when the apparatus is in operation. The reaction mixture containing such acetic acid is continuously drawn from the reactor 1 at a predetermined flow rate and introduced into the next evaporator 2 through the line 16.

The evaporator 2 is a unit configured to perform an evaporation step (flash step). The evaporation step is a step of partially evaporating the reaction mixture which is continuously introduced into the evaporator 2 through the line 16 (reaction mixture supply line), and separating the reaction mixture into a vapor stream (volatile phase) and a residual liquid stream (low volatile phase).

Evaporation may be done by reducing the pressure without heating the reaction mixture, or evaporation may be done by reducing the pressure while heating the reaction mixture. In the evaporation step, the temperature of the vapor stream is, for example, from 100 to 260° C., preferably from 120 to 200° C., the temperature of the residual liquid stream is, for example, from 80 to 200° C., preferably from 100 to 180° C., and the pressure in the tank is, for example, from 50 to 1000 kPa (absolute pressure).

The ratio of the vapor stream and the residual liquid stream separated in the evaporation step is, for example, from 10/90 to 50/50 (vapor stream/residual liquid stream) in terms of mass ratio. The vapor generated in this step contains, for example, methyl iodide, hydrogen iodide, water, methyl acetate, acetic acid, dimethyl ether, methanol, acetaldehyde, formic acid, and propionic acid, and alkyl iodides such as ethyl iodide, propyl iodide, butyl iodide, hexyl iodide, and decyl iodide. The vapor generated in this step is continuously drawn from the evaporator 2 into the line 17 (vapor stream discharge line).

A portion of the vapor stream drawn from the evaporator 2 is continuously introduced into the condenser 2a, and the other portion of the vapor stream is continuously introduced into the next distillation column 3 through the line 21. The acetic acid concentration of the vapor stream is, for example, from 40 to 85 mass % (preferably from 50 to 85 mass %), more preferably from 50 to 75 mass % (for example, from 55 to 75 mass %), and the methyl iodide concentration is, for example, from 2 to 50 mass % (preferably from 5 to 30 mass %), the water concentration is, for example, from 0.2 to 20 mass % (preferably from 1 to 15 mass %), and the methyl acetate concentration is, for example, from 0.2 to 50 mass % (preferably from 2 to 30 mass %). The hexyl iodide concentration of the vapor stream is, for example, from 0.1 to 10000 ppb by mass, usually from 0.5 to 1000 ppb by mass, and often from 1 to 100 ppb mass (for example, from 2 to 50 ppb by mass).

The residual liquid stream generated in this step includes catalysts and co-catalysts (for example, methyl iodide and lithium iodide) contained in the reaction mixture, and water, methyl acetate, acetic acid, formic acid, propionic acid and the like, which remain without being volatilized off in this step. The residual liquid stream generated in this step is continuously introduced from the evaporator 2 to the heat exchanger 2b through the line 18 by using the pump 57. The heat exchanger 2b cools the residual liquid stream from the evaporator 2. The cooled residual liquid stream is continuously introduced from the heat exchanger 2b into the reactor 1 through the line 19 and recycled. The lines 18 and 19 are collectively referred to as a residual liquid stream recycling line. The acetic acid concentration in the residual liquid stream is, for example, from 55 to 90 mass %, and preferably from 60 to 85 mass %.

The condenser 2a cools and partially condenses the vapor stream from the evaporator 2 to separate the vapor stream into a condensed component and a gas component. The condensed component contains, for example, methyl iodide, hydrogen iodide, water, methyl acetate, acetic acid, dimethyl ether, methanol, acetaldehyde, formic acid, and propionic acid, and is introduced from the condenser 2a into the reactor 1 through the lines 22 and 23 and recycled. The gas component contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid, and the gas component is supplied from the condenser 2a to the scrubber system 8 through the lines 20 and 15. The acetic acid formation reaction in the above reaction step is an exothermic reaction, and a portion of the heat accumulated in the reaction mixture is transferred to the vapor generated from the reaction mixture in the evaporation step (flash step). The condensed component formed by cooling the vapor in the condenser 2a is recycled to the reactor 1. That is, in this acetic acid production apparatus, the heat generated by the carbonylation reaction of methanol is efficiently removed by the condenser 2a.

The distillation column 3 is a unit configured to perform the first distillation step, and is classified as a so-called low-boiling component-removing column in the present embodiment. The first distillation step is a step of performing distillation of the vapor stream which is continuously introduced into the distillation column 3, and separating and removing the low boiling component. More specifically, in the first distillation step, the vapor stream is distilled to be separated into an overhead stream rich in at least one low boiling component selected from methyl iodide and acetaldehyde, and an acetic acid stream rich in acetic acid.

The distillation column 3 includes, for example, a rectification column such as a plate column and a packed column. When a plate column is adopted as the distillation column 3, the theoretical number of plates is, for example, from 5 to 50, and the reflux ratio is, for example, from 0.5 to 3000 depending on the theoretical number of plates. Inside the distillation column 3, the column top pressure is set to, for example, from 80 to 160 kPaG, and the column bottom pressure is set to be higher than the column top pressure, for example, from 85 to 180 kPaG. Inside the distillation column 3, the column top temperature is set to, for example, from 90 to 130° C., which is a temperature lower than the boiling point of acetic acid at the set column top pressure, and the column bottom temperature is set to, for example, from 120 to 165° C., which is a temperature equal to or higher than the boiling point of acetic acid at the set column bottom pressure (preferably from 125 to 160° C.).

The vapor stream from the evaporator 2 is continuously introduced into the distillation column 3 through the line 21, and the vapor as an overhead stream is continuously drawn into the line 24 from the top of the distillation column 3. From the bottom of the distillation column 3, a bottoms liquid is continuously drawn into the line 25. 3b indicates a reboiler. An acetic acid stream (first acetic acid stream; liquid) as a side stream is continuously drawn from the line 27 at a position which is located between the top and bottom of the distillation column 3.

The vapor drawn from the top of the distillation column 3 contains a larger amount of a component having a boiling point lower than that of acetic acid (a low boiling point component) as compared with the bottoms liquid and side stream from the distillation column 3, and contains, for example, methyl iodide, hydrogen iodide, water, methyl acetate, dimethyl ether, methanol, acetaldehyde, and formic acid. This vapor also contains acetic acid. Such vapor is continuously introduced into a condenser 3a through a line 24.

The condenser 3a cools and partially condenses the vapor stream from the distillation column 3 to separate the vapor stream into a condensed component and a gas component. The condensed component contains, for example, methyl iodide, hydrogen iodide, water, methyl acetate, acetic acid, dimethyl ether, methanol, acetaldehyde, and formic acid, and is continuously introduced from the condenser 3a through the line 28 to the decanter 4. The condensed component introduced into the decanter 4 is separated into an aqueous phase (upper phase) and an organic phase (methyl iodide phase; lower phase).

The aqueous phase includes water and, for example, methyl iodide, hydrogen iodide, methyl acetate, acetic acid, dimethyl ether, methanol, acetaldehyde, and formic acid. The organic phase contains, for example, methyl iodide and, for example, hydrogen iodide, water, methyl acetate, acetic acid, dimethyl ether, methanol, acetaldehyde, and formic acid.

In the present embodiment, a portion of the aqueous phase is refluxed to the distillation column 3 through the line 29, and the other portion of the aqueous phase is introduced into the reactor 1 through the lines 29, 30, and 23, and recycled. A portion of the organic phase is introduced into the reactor 1 through the lines 31 and 23, and recycled. The other portion of the organic phase and/or the other portion of the aqueous phase are/is introduced into the acetaldehyde separation and removal system 9 through the lines 31 and 50 and/or the lines 30 and 51. To the aqueous phase in the decanter 4, the first or second solution containing water may be recycled. The water in the first or second solution is merged with the aqueous phase and treated together with the aqueous phase.

In the acetaldehyde separation and removal step using the acetaldehyde separation and removal system 9, acetaldehyde contained in the organic phase and/or the aqueous phase is separated and removed by a known method, for example, distillation, extraction, or a combination thereof. The separated acetaldehyde is discharged out of the apparatus through line 53. In addition, useful components (for example, methyl iodide) contained in the organic phase and/or the aqueous phase are recycled to the reactor 1 through the lines 52 and 23, and reused.

Figure 7:
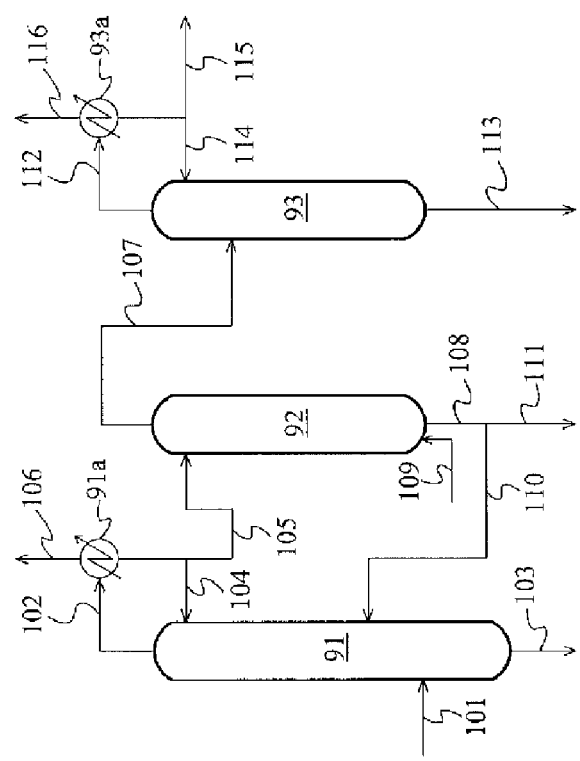
FIG. 7 is a schematic flow chart illustrating an example of an acetaldehyde separation and removal system.

FIG. 7 is a schematic flow chart illustrating an example of an acetaldehyde separation and removal system. According to this schematic flow chart, for example, in a case where the organic phase is treated in the acetaldehyde separation and removal step, the organic phase is supplied to a distillation column (first acetaldehyde removal column) 91 through a line 101 for distillation to be separated into an acetaldehyde-rich overhead stream (line 102) and a residual liquid stream rich in methyl iodide (line 103). The overhead stream is condensed by a condenser 91a, a portion of the condensed liquid is refluxed to the top of a distillation column 91 (line 104), and the other portion of the condensed liquid is supplied to an extraction column 92 (line 105).

The condensed liquid supplied to the extraction column 92 is extracted with water introduced from a line 109. The extracted liquid obtained by the extraction treatment is supplied to a distillation column (second acetaldehyde removal column) 93 through a line 107 and distilled to be separated into an acetaldehyde-rich overhead stream (line 112) and a water-rich residual liquid stream (line 113). Then, the acetaldehyde-rich overhead stream is condensed by a condenser 93a, a portion of the condensed liquid is refluxed to the top of a distillation column 93 (line 114), and the other portion of the condensed liquid is discharged out of the system (line 115).

Further, a residual liquid stream rich in methyl iodide, which is a bottoms liquid from the first acetaldehyde removal column 91, a methyl iodide-rich raffinate (line 108) obtained in the extraction column 92, and a water-rich residual liquid stream that is the bottoms liquid from the second acetaldehyde removal column 93 are recycled to reactor 1 through lines 103, 111, and 113, respectively, or recycled and reused at appropriate points in the process. For example, the methyl iodide-rich raffinate obtained in the extraction column 92 may be recycled to the distillation column 91 through a line 110. The liquid 113 is usually discharged to the outside as drainage. The gas (lines 106 and 116) that has not been condensed in the condensers 91a and 93a is absorbed by the scrubber system 8 or discarded.

In a case where the aqueous phase is treated in the acetaldehyde separation and removal step according to the schematic flow chart illustrated in FIG. 7, the aqueous phase is supplied to a distillation column (first acetaldehyde removal column) 91 through the line 101 for distillation, and separated into an acetaldehyde-rich overhead stream (line 102) and a water-rich residual liquid stream (line 103). The overhead stream is condensed by the condenser 91a, a portion of the condensed liquid is refluxed to the top of the distillation column 91 (line 104), and the other portion of the condensed liquid is supplied to the extraction column 92 (line 105).

The condensed liquid supplied to the extraction column 92 is extracted with water introduced from the line 109. The extracted liquid obtained by the extraction treatment is supplied to a distillation column (second acetaldehyde removal column) 93 through the line 107 and distilled, and is separated into an acetaldehyde-rich overhead stream (line 112) and a water-rich residual liquid stream (line 113). Then, the acetaldehyde-rich overhead stream is condensed by the condenser 93a, a portion of the condensed liquid is refluxed to the top of the distillation column 93 (line 114), and the other portion of the condensed liquid is discharged out of the system (line 115).

Further, the water-rich residual liquid stream which is the bottoms liquid from the first acetaldehyde removal column 91, the methyl iodide-rich raffinate (line 108) obtained in the extraction column 92, and the water-rich residual liquid stream which is the bottoms liquid from the second acetaldehyde removal column 93 are recycled to the reactor 1 through the lines 103, 111, 113, respectively, or recycled and reused at appropriate points in the process. For example, the methyl iodide-rich raffinate obtained in the extraction column 92 may be recycled to the distillation column 91 through line 110. The liquid 113 is usually discharged to the outside as drainage. The gas (lines 106 and 116) that has not been condensed in the condensers 91a and 93a is absorbed by the scrubber system 8 or discarded.

In addition to the above method, acetaldehyde derived from the process stream containing at least water, acetic acid (AC), methyl iodide (MeI), and acetaldehyde (AD) may be separated and removed by using extraction distillation. For example, while the organic phase and/or the aqueous phase (charge liquid) obtained by separating the process stream is supplied to the distillation column (extraction distillation column), an extraction solvent (usually water) is introduced into a concentration region (for example, a space between the top of the column and the charge liquid supply position) where methyl iodide and acetaldehyde are concentrated in the distillation column. Then, the liquid (extracted liquid) traveling downward from the concentration region is drawn as a side stream (side cut stream), this side stream is separated into an aqueous phase and an organic phase, and the aqueous phase is distilled, whereby acetaldehyde is discharged out of the system.

When a relatively large amount of water is present in the distillation column, the liquid traveling downward from the concentration region may be drawn as a side stream without introducing the extraction solvent into the distillation column. For example, a unit (such as a chimney tray) capable of receiving the liquid (extracted liquid) traveling downward from the concentration region may be arranged in the distillation column, and the liquid (extracted liquid) received by the unit may be drawn as a side stream.

The introduction position of the extraction solvent is preferably higher than the supply position of the charge liquid, and more preferably near the top of the column. The drawing position of the side stream is preferably lower than the introduction position of the extraction solvent and higher than the supply position of the charge liquid in the height direction of the column. According to this method, acetaldehyde can be drawn at a high concentration from the concentrate of methyl iodide and acetaldehyde by an extraction solvent (usually water), and the space between the introduction site and the side cut site of the extraction solvent is used as an extraction region, and acetaldehyde can be efficiently drawn with a small amount of extraction solvent. Therefore, for example, the number of plates of the distillation column can be significantly reduced and the vapor load can be reduced compared with the method of extracting the extracted liquid by extraction distillation from the bottom of the distillation column (extraction distillation column). In addition, using a small amount of extraction solvent, this method can make the ratio of methyl iodide to acetaldehyde (MeI/AD ratio) in the water extracted liquid smaller compared to the method of combining dealdehyde distillation and water extraction in FIG. 5, and acetaldehyde can be removed under conditions in which the loss of methyl iodide to the outside of the system can be suppressed.

The acetaldehyde concentration in the side stream is much higher than the acetaldehyde concentration in the charge liquid and the bottoms liquid (column bottom liquid). In addition, the ratio of acetaldehyde to methyl iodide in the side stream is larger than the ratio of acetaldehyde to methyl iodide in the charge liquid and the bottoms liquid.

The organic phase (methyl iodide phase) obtained by separating the side stream may be recycled to this distillation column. In this case, the position at which the organic phase obtained by separating the side stream is recycled is preferably lower than the position at which the side stream is drawn, and preferably higher than the position at which the charge liquid is supplied in the height direction of the column.

Further, a solvent miscible with the components (for example, methyl acetate, etc.) constituting the organic phase obtained by separating the process stream may be introduced into the distillation column (extraction distillation column). Examples of the miscible solvent include acetic acid and ethyl acetate. The position at which the miscible solvent is introduced is preferably lower than the position at which the side stream is drawn, and preferably higher than the position at which the charge liquid is supplied in the height direction of the column. In a case where the organic phase obtained by separating the side stream is recycled to the distillation column, the position at which the miscible solvent is introduced is preferably lower than the position at which the organic phase is recycled.

Recycling the organic phase obtained by separating the side stream into the distillation column or introducing the miscible solvent into the distillation column can reduce the concentration of methyl acetate in the extracted liquid drawn as a side stream, can reduce the concentration of methyl acetate in the aqueous phase obtained by separating the extracted liquid, and thus can suppress inclusion of methyl iodide into the aqueous phase.

The theoretical number of plates of the distillation column (extraction distillation column) is, for example, from 1 to 100, preferably from 2 to 50, more preferably from 3 to 30, and further preferably from 5 to 20. Therefore, acetaldehyde can be efficiently separated and removed with a smaller number of plates as compared with the 80 to 100 plates of a related art distillation column or extraction distillation column used for acetaldehyde removal.

The mass ratio of the flow rate of the extraction solvent and the flow rate of the charge liquid (organic phase and/or aqueous phase obtained by separating the process stream), (the extraction solvent)/(the charge liquid), may be chosen from the range of 0.0001/100 to 100/100, and is usually from 0.0001/100 to 20/100, preferably from 0.001/100 to 10/100, more preferably from 0.01/100 to 8/100, and still more preferably from 0.1/100 to 5/100.

The top temperature of the distillation column (extraction distillation column) is, for example, from 15 to 120° C., preferably from 20 to 90° C., more preferably from 20 to 80° C., and even more preferably from 25 to 70° C. The column top pressure is, for example, about 0.1 to 0.5 MPa (absolute pressure). Other conditions of the distillation column (extraction distillation column) may be the same as those of the distillation column and the extraction distillation column in a related art used for the acetaldehyde removal.

Figure 8:
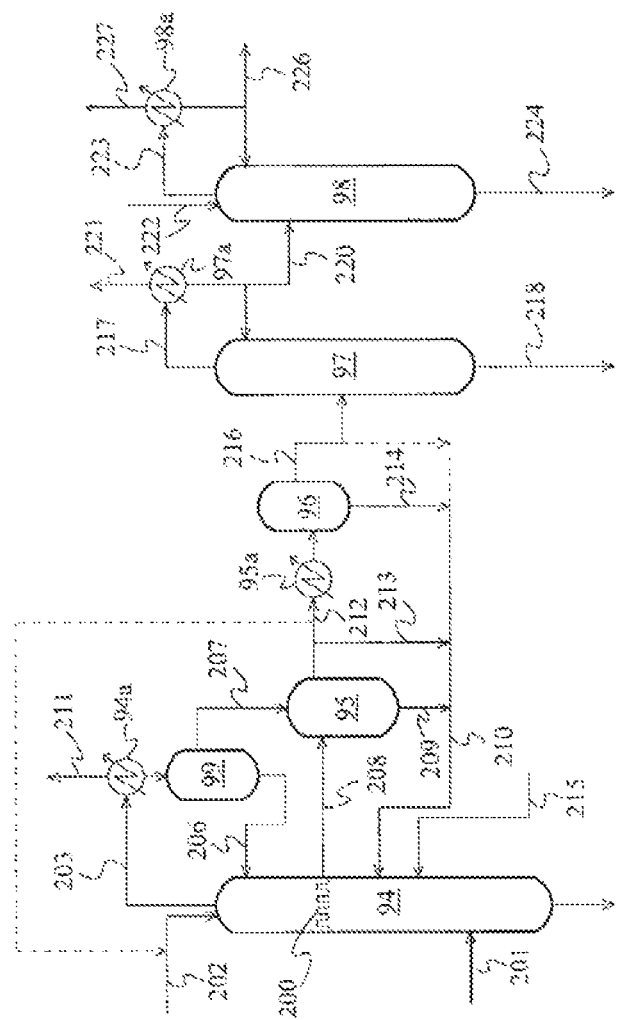
FIG. 8 is a schematic flow chart illustrating another example of an acetaldehyde separation and removal system.

FIG. 8 is a schematic flow chart illustrating an example of the acetaldehyde separation and removal system using the extraction distillation. In this example, the organic phase and/or the aqueous phase (charge liquid) obtained by separating the process stream is supplied to the middle stage (position between the top and bottom) of a distillation column 94 through a supply line 201, and water is introduced from the vicinity of the column top through a line 202, and extraction distillation is performed in the distillation column 94 (extraction distillation column).

A chimney tray 200 for receiving the liquid (extracted liquid) traveling downward from the concentration region where methyl iodide and acetaldehyde are concentrated in the distillation column 94 is arranged above the position at which the charge liquid is supplied in the distillation column 94. In this extraction distillation, preferably the entire amount of the liquid on a chimney tray 200 is drawn and introduced into a decanter 95 through a line 208, and separated.

The aqueous phase (including acetaldehyde) in the decanter 95 is introduced into a cooler 95a through a line 212 and cooled, and the methyl iodide dissolved in the aqueous phase is separated into two phases and separated by a decanter 96. The aqueous phase in the decanter 96 is supplied to a distillation column 97 (acetaldehyde removal column) through a line 216 for distillation, the vapor at the top of the column is led to a condenser 97a through a line 217 to be condensed, a portion of the condensed liquid (mainly acetaldehyde and methyl iodide) is refluxed to the top of the distillation column 97, and the rest of the condensed liquid is either discarded or supplied to a distillation column 98 (extraction distillation column) through a line 220.

Water is introduced from the vicinity of the top of the distillation column 98 through a line 222 and drawn and distilled. The vapor at the top of the column is led to the condenser 98a through a line 223 and condensed, a portion of the condensed liquid (mainly methyl iodide) is refluxed to the top of the column, and the rest is recycled to the reaction system through a line 226, but may be removed from the system. The organic phase (methyl iodide phase) in the decanter 95 is preferably recycled in its entirety through lines 209 and 210 to a position lower than the position of the chimney tray 200 in the distillation column 94. A portion of the aqueous phase of the decanter 95 and the organic phase of the decanter 96 are recycled to the distillation column 94 through lines 213 and 210 and lines 214 and 210, respectively, but may not be recycled. A portion of the aqueous phase of the decanter 95 may be used as an extraction solvent (water) in the distillation column 94. A portion of the aqueous phase of the decanter 96 may be recycled to the distillation column 94 through a line 210.

In some cases (for example, a case where the charge liquid contains methyl acetate), a miscible solvent (acetic acid, ethyl acetate, and the like) for the components (for example, methyl acetate) constituting the organic phase obtained by separating the process stream may be charged into the distillation column 94 through a line 215 to improve the distillation efficiency. The position at which the miscible solvent is supplied to the distillation column 94 is higher than the charge liquid supply section (a connecting section of the line 201) and lower than the connecting section of the recycling line 210. The bottoms liquid from the distillation column 94 is recycled to the reaction system.

The vapor at the top of the distillation column 94 is led to a condenser 94a through a line 203 and condensed, the condensed liquid is separated by a decanter 99, the organic phase is refluxed through a line 206 to the top of the distillation column 94, and the aqueous phase is led to a decanter 95 through a line 207.

The bottoms liquid (mainly water) from the distillation column 97 and the bottoms liquid (water containing a small amount of acetaldehyde) from the distillation column 98 (extraction distillation column) are removed from the system through lines 218 and 224, respectively, or recycled into the reaction system. The gas (lines 211, 221, and 227) that has not been condensed in the condensers 94a, 97a, and 98a is absorbed by the scrubber system 8 or discarded.

Figure 9:
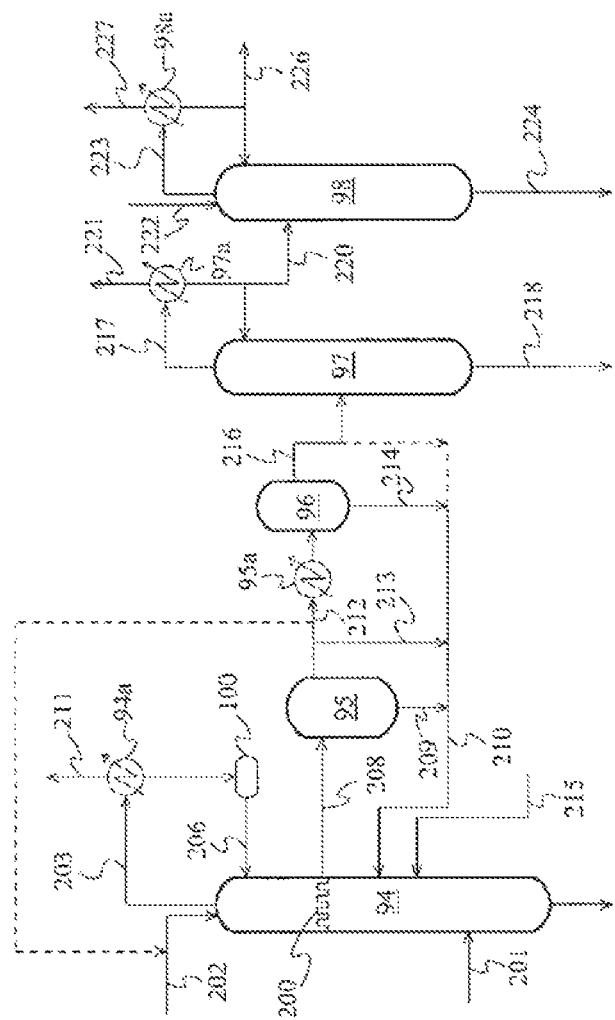
FIG. 9 is a schematic flow chart illustrating yet another example of an acetaldehyde separation and removal system.

FIG. 9 is a schematic flow chart illustrating another example of the acetaldehyde separation and removal system using the extraction distillation. In this example, the condensed liquid of the vapor at the top of the distillation column 94 is led to a hold tank 100, and the entire amount thereof is refluxed to the top of the distillation column 94 through the line 206. Other parts are the same as the example of FIG. 8.

Figure 10:
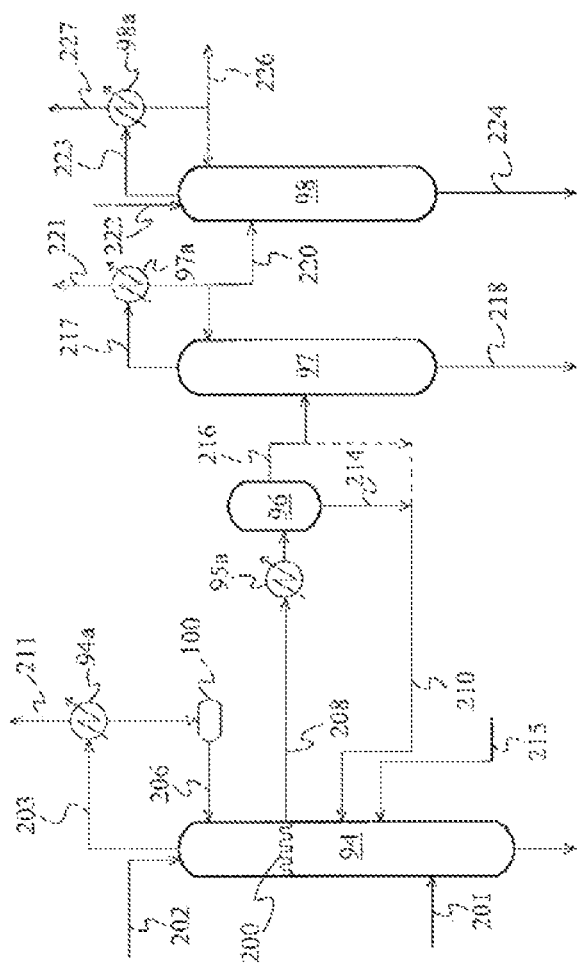
FIG. 10 is a schematic flow chart illustrating yet another example of an acetaldehyde separation and removal system.

FIG. 10 is a schematic flow chart illustrating still another example of the acetaldehyde separation and removal system using the extraction distillation. In this example, the entire amount of the liquid on the chimney tray 200 is drawn, introduced directly into the cooler 95a through the line 208 without passing through the decanter 95, cooled, and supplied to the decanter 96. Other parts are the same as the example of FIG. 9.

In FIG. 6, the gas component generated in the condenser 3a contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid, and is supplied from the condenser 3a to the scrubber system 8 through the lines 32 and 15. Methyl iodide, hydrogen iodide, water, methyl acetate, acetic acid, dimethyl ether, methanol, acetaldehyde, formic acid, and the like in the gas component that has reached the scrubber system 8 are absorbed by the absorbing liquid in the scrubber system 8. In a case where an absorbing liquid containing methanol or methyl acetate is used as the absorbing liquid in the absorption step, the first absorption step, or the second absorption step according to an embodiment of the present invention, hydrogen iodide produces methyl iodide by reaction with methanol or methyl acetate in the absorbing liquid. Then, the liquid component (overhead stream from the top of the distillation column 84) containing useful components such as methyl iodide can be recycled from the scrubber system 8 to the reactor 1 through the recycling lines 48 and 23 and reused.

The bottoms liquid drawn from the bottom of the distillation column 3 contains a large amount of components having a boiling point higher than that of acetic acid (high boiling point components) as compared with the overhead stream and the side stream from the distillation column 3, and contains, for example, propionic acid and the catalyst and co-catalyst accompanied by droplets. The bottoms liquid also contains acetic acid, methyl iodide, methyl acetate, water and the like. In the present embodiment, a portion of such bottoms liquid is continuously introduced into the evaporator 2 through the lines 25 and 26 and recycled, and the other portion of the bottoms liquid is continuously introduced into the reactor 1 through the lines 25 and 23 and recycled.

The first acetic acid stream continuously drawn from the distillation column 3 as a side stream is richer in acetic acid than the vapor stream continuously introduced into the distillation column 3. That is, the acetic acid concentration of the first acetic acid stream is higher than the acetic acid concentration of the vapor stream. The acetic acid concentration of the first acetic acid stream is, for example, from 90 to 99.9 mass %, and preferably from 93 to 99 mass %. In addition to acetic acid, the first acetic acid stream contains, for example, methyl iodide, hydrogen iodide, water, methyl acetate, dimethyl ether, methanol, acetaldehyde, formic acid, and alkyl iodides such as ethyl iodide, propyl iodide, butyl iodide, hexyl iodide, and decyl iodide.

The position at which the line 27 is connected with respect to the distillation column 3 may be higher than the position at which the line 21 is connected with respect to the distillation column 3 in the height direction of the distillation column 3 as illustrated in the schematic flow chart, but it may be lower than the position at which the line 21 is connected with respect to the distillation column 3, or may be at the same height as the position at which the line 21 is connected with respect to the distillation column 3. The first acetic acid stream from the distillation column 3 is continuously introduced into the next distillation column 5 through the line 27 at a predetermined flow rate. The first acetic acid stream drawn as a side stream of the distillation column 3, the bottom solution of the distillation column 3, or the condensed liquid of vapor at the bottom of the distillation column 3 can be continuously introduced into the distillation column 6 described later as they are without going through the distillation column 5 (dehydration step).

Potassium hydroxide may be supplied or added to the first acetic acid stream flowing through the line 27 through the line 55 (potassium hydroxide introduction line). Potassium hydroxide may be supplied or added as a solution such as an aqueous solution. Hydrogen iodide in the first acetic acid stream can be reduced by supplying or adding potassium hydroxide to the first acetic acid stream. Specifically, hydrogen iodide reacts with potassium hydroxide to produce potassium iodide and water. As a result, corrosion of equipment such as a distillation column due to hydrogen iodide can be reduced. Potassium hydroxide can be supplied or added to an appropriate place where hydrogen iodide is present in this process. Potassium hydroxide added during the process also reacts with acetic acid to produce potassium acetate.

The distillation column 5 is a unit configured to perform the second distillation step, and is classified as a so-called dehydration column in the present embodiment. The second distillation step is a step of distilling the first acetic acid stream continuously introduced into the distillation column 5 to further purify acetic acid.

The distillation column 5 includes, for example, a rectification column such as a plate column and a packed column. When adopting a plate column as the distillation column 5, the theoretical number of plates is, for example, from 5 to 50, and the reflux ratio is, for example, from 0.2 to 3000 depending on the theoretical number of plates. Inside the distillation column 5 in the second distillation step, the top pressure is set to, for example, from 150 to 250 kPaG, and the bottom pressure is set higher than the top pressure, for example, from 160 to 290 kPaG. Inside the distillation column 5 in the second distillation step, the column top temperature is set to, for example, from 130 to 160° C., which is higher than the boiling point of water and lower than the boiling point of acetic acid at the set top pressure, the column bottom temperature is set to, for example, from 150 to 175° C., which is a temperature equal to or higher than the boiling point of acetic acid at the set column bottom pressure.

From the top of the distillation column 5, the vapor which is an overhead stream is continuously drawn into the line 33. From the bottom of the distillation column 5, a bottoms liquid is continuously drawn into the line 34. 5b indicates a reboiler. A side stream (liquid or gas) may be continuously drawn into the line 34 from a position between the top and bottom of the distillation column 5.

The vapor drawn from the top of the distillation column 5 contains a large amount of components having a boiling point lower than that of acetic acid (low boiling point components) as compared with the bottoms liquid from the distillation column 5, and contains, for example, methyl iodide, hydrogen iodide, water, methyl acetate, acetic acid, dimethyl ether, methanol, acetaldehyde, and formic acid. Such vapor is continuously introduced into the condenser 5a through the line 33.

The condenser 5a cools and partially condenses the vapor from the distillation column 5 and separates the vapor into a condensed component and a gas component. The condensed component contains, for example, water and acetic acid. A portion of the condensed component is continuously refluxed from the condenser 5a to the distillation column 5 through the line 35. The other portion of the condensed component is continuously introduced from the condenser 5a into the reactor 1 through the lines 35, 36, and 23, and recycled. The gas component generated in the condenser 5a includes, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid, and is supplied from the condenser 5a to the scrubber system 8 through the lines 37 and 15. As described above, the gas component from the condenser 5a may be supplied to the scrubber system 8 without merging into the line 15. The hydrogen iodide in the gas component that reached the scrubber system 8 is absorbed by the absorbing liquid in the scrubber system 8, methyl iodide is produced by the reaction of hydrogen iodide in the absorbing liquid with methanol or methyl acetate, and then, the liquid component (overhead stream from the top of the distillation column 84) containing useful components such as methyl iodide is recycled from the scrubber system 8 to the reactor 1 through the recycling lines 48 and 23 and reused.

The bottoms liquid (or side stream) drawn from the bottom of the distillation column 5 contains a large amount of a component having a boiling point higher than that of acetic acid (high boiling point component) as compared with the above overhead stream from the distillation column 5, and contains, for example, acetic anhydride, propionic acid, acetate, iodide salts such as metal iodide salts derived from potassium iodide and corrosion metals, and the catalysts and co-catalysts accompanied by droplets. Examples of the acetate include metal acetates such as potassium acetate formed when an alkali such as potassium hydroxide is supplied to the line 27 or the like. Other examples include a metal acetate formed by acetic acid and corrosion metals such as metals generated and liberated on the inner wall of the constituent members of this acetic acid production apparatus. Examples of the iodide salt include potassium iodide formed when an alkali such as potassium hydroxide is supplied to the line 27 or the like. The bottoms liquid can also contain acetic acid. Such a bottoms liquid is continuously introduced into the next distillation column 6 as the second acetic acid stream through the line 34. The bottoms liquid (or side stream) drawn from the bottom of the distillation column 5 also contains the corrosion metal and the like described above, and a compound of iodine derived from the corrosive iodine and the corrosion metal and the like (iodide salt). In this embodiment, such a bottoms liquid is discharged to the outside of the acetic acid production apparatus.

The second acetic acid stream is richer in acetic acid than the first acetic acid stream that is continuously introduced into the distillation column 5. That is, the acetic acid concentration of the second acetic acid stream is higher than the acetic acid concentration of the first acetic acid stream. The acetic acid concentration of the second acetic acid stream is, for example, from 99.1 to 99.99 mass % as long as it is higher than the acetic acid concentration of the first acetic acid stream. As described above, the second acetic acid stream may contain, for example, propionic acid, hydrogen iodide, etc. in addition to acetic acid. In the present embodiment, in a case where the side stream is drawn, the position at which the side stream is drawn from the distillation column 5 is lower than the position at which the first acetic acid stream is introduced into the distillation column 5 in the height direction of the distillation column 5.

Potassium hydroxide can be supplied or added to the second acetic acid stream passing through the line 34 through the line 56 (potassium hydroxide introduction line). Potassium hydroxide may be supplied or added as a solution such as an aqueous solution. Hydrogen iodide in the second acetic acid stream can be reduced by supplying or adding potassium hydroxide to the second acetic acid stream. Specifically, hydrogen iodide reacts with potassium hydroxide to produce potassium iodide and water. As a result, corrosion of equipment such as a distillation column due to hydrogen iodide can be reduced.

The distillation column 6 is a unit configured to perform the third distillation step, and is classified as a so-called high-boiling component-removing column in the present embodiment. The third distillation step is a step of purifying the second acetic acid stream continuously introduced into the distillation column 6 to further purify acetic acid.

The distillation column 6 includes, for example, a rectification column such as a plate column and a packed column. When adopting a plate column as the distillation column 6, the theoretical number of plates is, for example, from 5 to 50, and the reflux ratio is, for example, from 0.2 to 3000 depending on the theoretical number of plates. Inside the distillation column 6 in the third distillation step, the top pressure is set to, for example, from −100 to 150 kPaG, and the bottom pressure is set to be higher than the top pressure, for example, from −90 to 180 kPaG. Inside the distillation column 6 in the third distillation step, the column top temperature is set to, for example, from 50 to 150° C., which is higher than the boiling point of water and lower than the boiling point of acetic acid at the set top pressure, and the column bottom temperature is set to, for example, from 70 to 160° C., which is higher than the boiling point of acetic acid at the set column bottom pressure.

From the top of the distillation column 6, the vapor, which is an overhead stream, is continuously drawn into the line 38. From the bottom of the distillation column 6, a bottoms liquid is continuously drawn into the line 39. 6b indicates a reboiler. A side stream (liquid or gas) is continuously drawn into the line 46 from the position between the top and bottom of the distillation column 6. In the height direction of the distillation column 6, the position at which the line 46 is connected with respect to the distillation column 6 may be higher than the position at which the line 34 is connected with respect to the distillation column 6, as shown in the figure, but may be lower than the position at which the line 34 is connected with respect to the distillation column 6, or may be at the same height as the position at which the line 34 is connected with respect to the distillation column 6.

The vapor drawn from the top of the distillation column 6 contains a large amount of components having a boiling point lower than that of acetic acid (low boiling point components) as compared with the bottoms liquid from the distillation column 6, and in addition to acetic acid, for example, methyl iodide, hydrogen iodide, water, methyl acetate, dimethyl ether, methanol, and formic acid. Such vapor is continuously introduced into a condenser 6a through the line 38.

The condenser 6a cools and partially condenses the vapor from the distillation column 6 to separate the vapor into a condensed component and a gas component. In addition to acetic acid, the condensed component contains, for example, methyl iodide, hydrogen iodide, water, methyl acetate, dimethyl ether, methanol, formic acid and the like. At least a portion of the condensed component is continuously refluxed from the condenser 6a through the line 40 to the distillation column 6. A portion of the condensed component (distillate) can be recycled from the condenser 6a through the lines 40, 41 and 42 to the first acetic acid stream in the line 27 before being introduced into the distillation column 5. Along with or instead of this operation, a portion of the condensed component (distillate) can be recycled from the condenser 6a through the lines 40, 41, 43 to the vapor stream in the line 21 before being introduced into the distillation column 3.

A portion of the condensed component (distillate) may be recycled from the condenser 6a to the reactor 1 through the lines 40, 44, and 23. Further, as described above, a portion of the distillate from the condenser 6a can be supplied to the scrubber system 8 and used as an absorbing liquid in the system. In the scrubber system 8, the gas component after absorbing the useful components is discharged to the outside of the apparatus, and the liquid component containing useful components (overhead stream from the top of the distillation column 84) is introduced or recycled from the scrubber system 8 into the reactor 1 through the recycling lines 48 and 23, and reused. In addition, a portion of the distillate from the condenser 6a may be led to various pumps (not illustrated) operating in the apparatus through a line (not illustrated) and used as a sealing liquid for the pump. Furthermore, a portion of the distillate from the condenser 6a may be constantly drawn from the device through a drawing line attached to the line 40, or may be drawn from the apparatus when necessary.

In a case where a portion of the condensed component (distillate) is removed from the distillation treatment system in the distillation column 6, the amount of the distillate (distillated amount) is, for example, from 0.01 to 30 mass %, and is preferably from 0.1 to 10 mass %, more preferably from 0.3 to 5 mass %, and even more preferably from 0.5 to 3 mass % of the condensed liquid generated in the condenser 6a. On the other hand, the gas component generated in the condenser 6a contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid, and is supplied from the condenser 6a to the scrubber system 8 through the lines 45 and 15. As described above, the gas component from the condenser 6a may be supplied to the scrubber system 8 without merging with the line 15.

The bottoms liquid drawn from the bottom of the distillation column 6 through the line 39 contains a large amount of components having a boiling point higher than that of acetic acid (high boiling point components) as compared with the overhead stream from the distillation column 6, and contains, for example, acetate, acetic anhydride, propionic acid, and the like. Examples of the acetate include potassium acetate formed when an alkali such as potassium hydroxide is supplied to the line 34 or the like. Other examples include metal acetate formed by acetic acid and corrosion metals such as metals generated and liberated on the inner wall of the constituent members of the acetic acid production apparatus. The bottoms liquid drawn from the bottom of the distillation column 6 through the line 39 further contains the corrosion metal and the like, and a compound of iodine derived from the corrosive iodine and the corrosion metal and the like. In this embodiment, the bottoms liquid is discharged to the outside of the acetic acid production apparatus.

The side stream continuously drawn from the distillation column 6 to the line 46 is continuously introduced into the next ion exchange resin column 7 as a third acetic acid stream. This third acetic acid stream is richer in acetic acid than the second acetic acid stream that is continuously introduced into the distillation column 6. That is, the acetic acid concentration of the third acetic acid stream is higher than the acetic acid concentration of the second acetic acid stream. The acetic acid concentration of the third acetic acid stream is, for example, from 99.8 to 99.999 mass % as long as it is higher than the acetic acid concentration of the second acetic acid stream. In the present embodiment, the position at which the side stream is drawn from the distillation column 6 is higher in the height direction of the distillation column 6 than the position at which the second acetic acid stream is introduced into the distillation column 6. In another embodiment, the position at which the side stream is drawn from the distillation column 6 is at the same height as, or lower than, the position at which the second acetic acid stream is introduced into the distillation column 6 in the height direction of the distillation column 6. The distillation column 6 may be replaced with a pot still (evaporator), and the distillation column 6 may be omitted if impurities are sufficiently removed by the distillation column 5.

The ion exchange resin column 7 is a purification unit configured to perform an adsorption removal step. The adsorption removal step is a step of adsorbing and removing mainly alkyl iodide (for example, ethyl iodide, propyl iodide, butyl iodide, and hexyl iodide) contained in a trace amount in the third acetic acid stream continuously introduced into the ion exchange resin column 7 to further purify the acetic acid.

In the ion exchange resin column 7, an ion exchange resin having an adsorptive ability to alkyl iodide is filled in the column to form an ion exchange resin bed. Examples of the ion exchange resin include a cation exchange resin in which some of the dissociative protons in the sulfonic acid group, carboxyl group, phosphonic acid group, and the like, which are the exchange groups, are replaced with a metal such as silver or copper. In the adsorption removal step, for example, a third acetic acid stream (liquid) flows through the inside of the ion exchange resin column 7 filled with such an ion exchange resin, and in the flow process, impurities such as alkyl iodide in the third acetic acid stream are adsorbed on the ion exchange resin and removed from the third acetic acid stream. In the ion exchange resin column 7 in the adsorption removal step, the internal temperature is, for example, from 18 to 100° C., and the flow rate of acetic acid stream [the amount of treated acetic acid per 1 m$^3$ (m$^3$/h) of the resin volume] is, for example, from 3 to 15 m$^3$/h·m$^3$ (resin volume).

A fourth acetic acid stream is continuously drawn from the lower end of the ion exchange resin column 7 to the line 47. The acetic acid concentration of the fourth acetic acid stream is higher than the acetic acid concentration of the third acetic acid stream. That is, the fourth acetic acid stream is richer in acetic acid than the third acetic acid stream that is continuously introduced into the ion exchange resin column 7. The acetic acid concentration of the fourth acetic acid stream is, for example, from 99.9 to 99.999 mass % or greater as long as it is higher than the acetic acid concentration of the third acetic acid stream. In this production method, this fourth acetic acid stream can be stored in a product tank (not illustrated).

In this acetic acid production apparatus, a so-called product column or finishing column, which is a distillation column, may be provided as a purification unit for further purifying the fourth acetic acid stream from the ion exchange resin column 7. When such a product column is provided, the product column includes, for example, a rectification column such as a plate column and a packed column. When a plate column is adopted as the product column, the theoretical number of plates is, for example, from 5 to 50, and the reflux ratio is, for example, from 0.5 to 3000 depending on the theoretical number of plates. Inside the product column in the refining process, the column top pressure is set to, for example, from −195 to 150 kPaG, and the column bottom pressure is set to be higher than the column top pressure, for example, from −190 to 180 kPaG. Inside the product column, the column top temperature is set to, for example, from 50 to 150° C., which is higher than the boiling point of water and lower than the boiling point of acetic acid at the set top pressure, and the column bottom temperature is set to, for example, from 70 to 160° C., which is higher than the boiling point of acetic acid at the set column bottom pressure. The product column or finishing column can be replaced with a simple distiller (evaporator).

In a case where the product column is provided, all or portion of the fourth acetic acid stream (liquid) from the ion exchange resin column 7 is continuously introduced into the product column. From the top of the column of such a product column, the vapor is continuously drawn as an overhead stream including trace amounts of low boiling point components (for example, methyl iodide, water, methyl acetate, dimethyl ether, crotonaldehyde, acetaldehyde, and formic acid). This vapor is separated into a condensed component and a gas component by a predetermined condenser.

A portion of the condensed component may be continuously refluxed to the product column, the other portion of the condensed component may be recycled to reactor 1, discarded outside the system, or both, and the gas component is supplied to the scrubber system 8. A bottoms liquid containing a trace amount of high boiling point components is continuously drawn from the bottom of the product column, and the bottoms liquid is recycled, for example, into the second acetic acid stream in the line 34 before being introduced into the distillation column 6. A side stream (liquid) is continuously drawn as a fifth acetic acid stream from the position between the top and bottom of the product column. The position at which the side stream is drawn from the product column is lower than, for example, the position at which the fourth acetic acid stream is introduced into the product column in the height direction of the product column.

The fifth acetic acid stream is richer in acetic acid than the fourth acetic acid stream that is continuously introduced into the product column. That is, the acetic acid concentration of the fifth acetic acid stream is higher than the acetic acid concentration of the fourth acetic acid stream. The acetic acid concentration of the fifth acetic acid stream is, for example, from 99.9 to 99.999 mass % or greater as long as it is higher than the acetic acid concentration of the fourth acetic acid stream. This fifth acetic acid stream is stored, for example, in a product tank (not illustrated). The ion exchange resin column 7 may be installed downstream of the product column to treat the acetic acid stream from the product column, instead of (or in addition to) installing it downstream of the distillation column 6.

EXAMPLES

Hereinafter, the present invention will be described in more detail based on examples, but the present invention is not limited by these examples. The %, ppm and ppb are all mass-based. The hydrogen iodide concentration is a value obtained by the subtraction method.

Comparative Example 1

An experiment was conducted using the scrubber system shown in FIG. 11(a). The high-pressure charge gas (1) and the low-pressure charge gas (5) were charged into the high-pressure absorption column A (theoretical number of plates; 5) and the low-pressure absorption column B (theoretical number of plates; 5), respectively, circulating acetic acid as an absorbent was introduced from the tops of both absorption columns, acetic acid was sprayed from the upper portion of the absorption column with a dispersion plate to absorb the condensable gas containing an iodine compound, thus an absorption step was performed. Then, the absorbing liquid was drawn from the bottoms from the absorption column. The high-pressure offgas (3) from the top of the high-pressure absorption column A and the low-pressure offgas (7) from the top of the low-pressure absorption column B were merged and discharged out of the system. The charge liquid (9) obtained by merging the bottoms liquid from the high-pressure absorption column A (4) and the bottoms liquid from the low-pressure absorption column B (8) was charged in the central part (upper part theoretical number of plates: 2.5, lower part theoretical number of plates: 2.5) of the distillation column C (theoretical number of plates: 5) where the stripping step is performed, vapor heating was performed in the distillation column C to concentrate a low boiling component other than acetic acid on the column top to obtain an overhead stream (10), which was distilled off at a reflux ratio (reflux amount/distillation amount) 1 and recycled to the reactor. Acetic acid (11) after diffusion was drawn from the distillation column C bottoms, cooled, replenished with a new portion of acetic acid (12), and then circulated and used as absorbing liquids (2) and (6) in the high-pressure absorption column and the low-pressure absorption column. For the two absorption columns and the distillation column, a structured packing "Merapack 250X" available from Thruzer Chemtech Ltd. was used. In this experiment, the bottoms liquid from the distillation column was not drawn from the system. The concentration of hydrogen iodide in the bottoms liquid from the distillation column was 15 ppm by mass. Table 1 gives the flow rates and the concentrations of various components in the above (1) to (11).

In each table, "AD" indicates acetaldehyde, "MeI" indicates methyl iodide, "MA" indicates methyl acetate, "AC" indicates acetic acid, and "PA" indicates propionic acid. The symbol "-" in the table indicates that the concentration of the component was not measured. "Other" may include a case where the following components may have been present: the components whose concentrations were not measured as shown in each table; substances that worsen the potassium permanganate test value (potassium permanganate time) such as methanol, dimethyl ether, propionic acid, and crotonaldehyde; and organic iodine compounds.

A metal test piece was placed in the bottom liquid of the distillation column C, and the above experiment was continuously performed at 147° C. for 500 hours. After the experiment was completed, the test piece was taken out and the corrosiveness was evaluated in terms of the thickness reduction rate per year using the mass change. As test pieces, various material test pieces including zirconium (Zr), Hastelloy C ("HC276" available from Oda Koki Co., Ltd.), which was a nickel-based alloy, SUS316 ("SUS316" available from Umetoku Inc.), and SUS304 ("SUS304" available from Umetoku Inc.) (size: 36 mm×25 mm×2.5 mm) were used. As shown in Table 5, it can be seen that only zirconium indicated the perfect corrosion resistance, at the corrosiveness of less than 0.05 mm/Y, and low-grade materials such as Hastelloy or lower cannot be used. In the experiment, in addition to the test piece above, SUS304 (available from Umetoku Inc.) of the same size was placed in the bottoms liquids from the high-pressure absorption column A and the low-pressure absorption column B in the low temperature region, and an evaluation was performed; both results were the corrosiveness of less than 0.05 mm/Y indicating perfect corrosion resistance, and there was no problem with these tests.

TABLE 1

| | | (1) High-pressure charge gas | (2) High-pressure absorption column absorbing liquid | (3) High-pressure offgas | (4) High-pressure absorption column bottoms liquid | (5) Low-pressure charge gas | (6) Low-pressure absorption column absorbing liquid |
|---|---|---|---|---|---|---|---|
| Flow rate | Part by mass | 1.2 | 18.6 | 0.9 | 18.9 | 16.0 | 74.6 |
| $H_2$ | mass % | 0.3 | — | 0.4 | — | 0.5 | — |
| CO | mass % | 67.1 | — | 86.2 | — | 42.2 | — |
| $CO_2$ | mass % | 0.9 | — | 1.2 | — | 4.7 | — |
| $CH_4$ | mass % | 3.0 | — | 3.9 | — | 5.3 | — |
| $N_2$ | mass % | 4.8 | — | 6.1 | — | 5.7 | — |
| AD | mass % | 0.3 | — | — | 0.0 | 0.1 | — |
| MeI | mass % | 21.4 | 0.0 | — | 1.4 | 37.3 | 0.0 |
| MA | mass % | — | — | — | — | 1.9 | — |
| $H_2O$ | mass % | 0.1 | 0.3 | — | 0.3 | 0.1 | 0.3 |
| AC | mass % | 0.1 | 99.0 | 0.1 | 97.6 | 0.0 | 99.0 |
| Heptane | mass % | 0.0 | 0.0 | 0.0 | 0.0 | 0.0 | 0.0 |
| HI | mass % | 0.0111 | 0.0014 | 0.0029 | 0.0020 | 0.0084 | 0.0014 |
| Other | mass % | 2.0 | 0.8 | 2.1 | 0.8 | 2.1 | 0.8 |
| Total | mass % | 100.0 | 100.0 | 100.0 | 100.0 | 100.0 | 100.0 |
| TEMPERATURE | ° C. | 26.0 | 28.8 | 35.9 | 33.2 | 14.8 | 23.5 |
| Pressure | KPaG | 2760 | 2800 | 2750 | 2750 | 128 | 122 |

| | | (7) Low-pressure offgas | (8) Low-pressure absorption column bottoms liquid | (9) Distillation column charge liquid | (10) Distillate from distillation column | (11) Bottoms liquid from distillation column |
|---|---|---|---|---|---|---|
| Flow rate | Part by mass | 9.5 | 81.1 | 100.0 | 11.1 | 88.9 |
| $H_2$ | mass % | 0.8 | 0.0 | 0.0 | 0.0 | — |
| CO | mass % | 71.2 | 0.0 | 0.0 | 0.0 | — |
| $CO_2$ | mass % | 8.0 | 0.0 | 0.0 | 0.0 | — |
| $CH_4$ | mass % | 9.0 | 0.0 | 0.0 | 0.0 | — |
| $N_2$ | mass % | 9.6 | 0.0 | 0.0 | 0.0 | — |
| AD | mass % | — | 0.0 | 0.0 | 0.2 | — |
| MeI | mass % | — | 7.3 | 6.2 | 56.1 | — |
| MA | mass % | — | 0.4 | 0.3 | 2.8 | — |
| $H_2O$ | mass % | — | 0.3 | 0.3 | 0.2 | 0.3 |
| AC | mass % | 0.0 | 91.0 | 92.3 | 38.4 | 99.0 |
| Heptane | mass % | 0.0 | 0.0 | 0.0 | 0.0 | 0.0 |
| HI | mass % | 0.0028 | 0.0026 | 0.0025 | 0.0106 | 0.0015 |
| Other | mass % | 1.4 | 1.0 | 0.9 | 2.3 | 0.8 |
| Total | mass % | 100.0 | 100.0 | 100.0 | 100.0 | 100.0 |
| TEMPERATURE | ° C. | 24.0 | 32.4 | 24.0 | 24.0 | 146.6 |
| Pressure | KPaG | 122 | 123 | 122 | 119 | 133 |

Comparative Example 2

An experiment was conducted using the scrubber system shown in FIG. 11(b). The high-pressure charge gas (1) and the low-pressure charge gas (5) were charged into the high-pressure absorption column A (theoretical number of plates; 5) and the low-pressure absorption column B (theoretical number of plates; 5), respectively, circulating water was introduced from the tops of both absorption columns, water was sprayed from the upper portion of the absorption column with a dispersion plate to absorb the condensable gas containing an iodine compound, thus a first absorption step was performed. Then, the absorbing liquids (4) and (8) were drawn from the bottoms from the absorption column. After merging the absorbing liquids (4) and (8) from both the drawn absorption column bottoms, a portion of the absorbing liquid was withdrawn (9) and recycled to the reactor via a decanter configured to store the overhead stream condensed liquid from the low-boiling component-removing column. The high-pressure offgas (3) from the top of the high-pressure absorption column A and the low-pressure offgas (7) from the top of the low-pressure absorption column B were merged and charged into the bottom of the low-pressure absorption column D (theoretical number of plates: 5) (12), circulating acetic acid was introduced from the top of the low-pressure absorption column D, sprayed from the upper portion of the absorption column with a dispersion plate, the condensable gas containing an iodine compound was absorbed, thus the second absorption step was performed. Then, the absorbing liquid (15) was drawn from the absorption column bottoms. The low-pressure absorption column D bottoms liquid (15) was charged into the central portion (upper part theoretical number of plates: 2.5, lower part theoretical number of plates: 2.5) of the distillation column C (theoretical number of plates: 5) where the stripping step was performed, vapor heating was performed in the distillation column to concentrate a low boiling component other than acetic acid on the top of the column to produce an overhead stream (16), which was distilled off at a reflux ratio (reflux amount/distillation amount) 5 and recycled to the reactor. A solution (17) mainly containing acetic acid after diffusion was drawn from the distillation column bottoms, cooled, replenished with new acetic acid (19), and then circulated and used as an absorbing liquid (13) in the low-pressure absorption column D. The solution (17) was not discharged from the system (18). For each of the three absorption columns and the distillation column, a structured packing "Merapack 250X" (available from Thruzer Chemtech Ltd.) was used. In the present experiment, the bottoms liquid from the distillation column C was not drawn from the system. The concentration of hydrogen iodide in the bottoms liquid from the distillation column was below the detection limit. Table 2 gives the flow rates and the concentrations of various components in the above (1) to (9) and (11) to (17).

A metal test piece was placed in the bottom liquid of the distillation column C, and the above experiment was continuously performed at 147° C. for 500 hours. After the experiment was completed, the test piece was taken out and the corrosiveness was evaluated in terms of the thickness reduction rate per year using the mass change. The test piece used is the same as in Comparative Example 1. As given in Table 5, zirconium and HC276 showed perfect corrosion resistance, corrosiveness of less than 0.05 mm/Y. However, the results of the low-grade materials such as SUS were 0.11 mm/Y (SUS316) and 0.21 mm/Y (SUS304), indicating that advanced corrosion compared to 0.04 mm/Y (SUS316) and 0.05 mm/Y (SUS304) of Example 1, and that corrosion has advanced beyond the index of perfect corrosion resistance of 0.05 mm/Y. Since partial corrosion did not occur in Comparative Example 2, good results were obtained when compared with Comparative Example 1 with partial corrosion. In the experiment, in addition to the test piece above, SUS304 (available from Umetoku Inc.) of the same size was placed in the bottoms liquids from the high-pressure absorption column A and the low-pressure absorption column B in the low temperature region, and an evaluation was performed; both results were the corrosiveness of less than 0.05 mm/Y indicating perfect corrosion resistance, and there was no problem with these tests.

TABLE 2

|  |  | (1) High-pressure charge gas | (2) High-pressure absorption column absorbing liquid | (3) High-pressure offgas | (4) High-pressure absorption column bottoms liquid | (5) Low-pressure charge gas | (6) Low-pressure absorption column absorbing liquid | (7) Low-pressure offgas | (8) Low-pressure absorption column bottoms liquid | Merged liquid of (4) and (8) |
|---|---|---|---|---|---|---|---|---|---|---|
| Flow rate | Part by mass | 1.2 | 35.8 | 1.5 | 35.5 | 16.0 | 143.1 | 15.7 | 143.4 | 178.9 |
| $H_2$ | mass % | 0.3 | — | 0.2 | — | 0.5 | — | 0.5 | — | — |
| CO | mass % | 67.1 | — | 53.4 | — | 42.2 | — | 43.1 | — | — |
| $CO_2$ | mass % | 0.9 | — | 0.7 | — | 4.7 | — | 4.8 | — | — |
| $CH_4$ | mass % | 3.0 | — | 2.4 | — | 5.3 | — | 5.4 | — | — |
| $N_2$ | mass % | 4.8 | — | 3.8 | — | 5.7 | — | 5.8 | — | — |
| AD | mass % | 0.3 | — | 0.2 | — | 0.1 | — | 0.1 | — | — |
| MeI | mass % | 21.4 | 0.6 | 16.9 | 0.6 | 37.3 | 3.6 | 38.0 | 0.6 | 0.6 |
| MA | mass % | — | 0.3 | 1.3 | 0.3 | 1.9 | 0.3 | 1.8 | 0.3 | 0.3 |
| $H_2O$ | mass % | 0.1 | 97.9 | 1.0 | 98.7 | 0.1 | 97.9 | 0.0 | 97.7 | 97.9 |
| AC | mass % | 0.1 | 0.2 | 0.0 | 0.2 | 0.0 | 0.2 | 0.0 | 0.2 | 0.2 |
| Heptane | mass % | — | — | — | — | — | — | — | — | — |
| HI | mass % | 0.0111 | 0.1423 | 0.0001 | 0.1440 | 0.0084 | 0.1423 | 0.0001 | 0.1429 | 0.1431 |
| Other | mass % | 2.0 | 0.8 | 20.0 | 0.1 | 2.1 | 0.8 | 0.3 | 1.0 | 0.9 |
| Total | mass % | 100.0 | 100.0 | 100.0 | 100.0 | 100.0 | 100.0 | 100.0 | 100.0 | 100.0 |
| TEMPERATURE | ° C. | 25.8 | 28.6 | 35.5 | 33.0 | 14.2 | 23.2 | 23.9 | 32.2 | 25.1 |
| Pressure | KPaG | 2750 | 2990 | 2740 | 2740 | 127 | 121 | 121 | 122 | 121 |

|  |  | (9) Extraction of first absorption bottoms | (11) Circulation of first absoibent | (12) Second absorption charge gas | (13) Second absorbent | (14) Second absorption offgas | (15) Second absorption bottoms liquid | (16) Distillate from distillation column | (17) Bottoms liquid from distillation column |
|---|---|---|---|---|---|---|---|---|---|
| Flow rate | Part by mass | 1.0 | 178.9 | 17.2 | 94.7 | 10.5 | 101.3 | 15.1 | 86.2 |
| $H_2$ | mass % | — | — | 0.5 | — | 0.8 | 0.0 | 0.0 | — |
| CO | mass % | — | — | 44.0 | — | 72.0 | 0.0 | 0.0 | — |
| $CO_2$ | mass % | — | — | 4.5 | — | 7.3 | 0.0 | 0.0 | — |
| $CH_4$ | mass % | — | — | 5.2 | — | 8.4 | 0.0 | 0.0 | — |
| $N_2$ | mass % | — | — | 5.6 | — | 9.2 | 0.0 | 0.0 | — |

TABLE 2-continued

| | | | | | | | | | |
|---|---|---|---|---|---|---|---|---|---|
| AD | mass % | — | — | 0.2 | — | 0.0 | 0.0 | 0.2 | — |
| MeI | mass % | 0.6 | 0.6 | 36.2 | 0.0 | 0.0 | 6.1 | 41.2 | — |
| MA | mass % | 0.3 | 0.3 | 1.8 | — | 0.0 | 0.3 | 2.0 | — |
| $H_2O$ | mass % | 97.9 | 97.0 | 0.1 | 0.2 | 0.0 | 0.2 | 0.2 | 0.2 |
| AC | mass % | 0.2 | 0.2 | 0.0 | 99.1 | 0.0 | 92.6 | 55.7 | 99.0 |
| Heptane | mass % | — | — | — | — | — | — | — | — |
| HI | mass % | 0.1431 | 0.1423 | 0.0001 | — | 0.0000 | 0.0000 | 0.0001 | 0.0000 |
| Other | mass % | 0.9 | 0.8 | 2.0 | 0.7 | 2.2 | 0.8 | 0.8 | 0.7 |
| Total | mass % | 100.0 | 100.0 | 100.0 | 100.0 | 100.0 | 100.0 | 100.0 | 100.0 |
| TEMPERATURE | ° C. | 23.7 | 32.1 | 25.0 | 33.2 | 31.8 | 32.9 | 32.9 | 146.5 |
| Pressure | KPaG | 121 | 121 | 121 | 135 | 119 | 123 | 119 | 133 |

Comparative Example 3

The experiment was performed in the same manner as in Comparative Example 2 except that the absorption step in the high-pressure absorption column A was not performed. Table 3 shows the flow rates and the concentrations of various components in the above (5) to (9) and (11) to (17).

A metal test piece was placed in the bottom liquid of the distillation column C, and the above experiment was continuously performed at 147° C. for 500 hours. After the experiment was completed, the test piece was taken out and the corrosiveness was evaluated in terms of the thickness reduction rate per year using the mass change. The test piece used is the same as in Comparative Example 1. As given in Table 5, zirconium and HC276 showed perfect corrosion resistance, corrosiveness of less than 0.05 mm/Y. However, the results of the low-grade materials such as SUS were 0.12 mm/Y (SUS316) and 0.25 mm/Y (SUS304), indicating that advanced corrosion compared to 0.04 mm/Y (SUS316) and 0.05 mm/Y (SUS304) of Example 1, and that corrosion has advanced beyond the index of perfect corrosion resistance of 0.05 mm/Y. Since partial corrosion did not occur in Comparative Example 3, good results were obtained when compared with Comparative Example 1 with partial corrosion. In the experiment, in addition to the test piece above, SUS304 (available from Umetoku Inc.) of the same size was placed in the bottoms liquids from the high-pressure absorption column A and the low-pressure absorption column B in the low temperature region, and an evaluation was performed; both results were the corrosiveness of less than 0.05 mm/Y indicating perfect corrosion resistance, and there was no problem with these tests.

TABLE 3

| | | (5) Low-pressure charge gas | (6) Low-pressure absorption column absorbing liquid | (7) Low-pressure offgas | (8) Low-pressure absorption column bottoms liquid | Merged liquid of (4) and (8) | (9) Drawing from first absorption bottoms |
|---|---|---|---|---|---|---|---|
| Flow rate | Part by mass | 16.0 | — | 16.0 | 143.4 | 143.4 | 1.0 |
| $H_2$ | mass % | 0.5 | — | 0.5 | — | — | — |
| CO | mass % | 42.2 | — | 42.3 | — | — | — |
| $CO_2$ | mass % | 4.7 | — | 4.7 | — | — | — |
| $CH_4$ | mass % | 5.3 | — | 5.3 | — | — | — |
| $N_2$ | mass % | 5.7 | — | 5.7 | — | — | — |
| AD | mass % | 0.1 | — | 0.1 | — | — | — |
| MeI | mass % | 37.3 | 0.6 | 37.3 | 0.6 | 0.6 | 0.6 |
| MA | mass % | 1.9 | 0.3 | 1.9 | 0.3 | 0.3 | 0.3 |
| $H_2O$ | mass % | 0.1 | 97.7 | 0.1 | 97.7 | 97.8 | 97.8 |
| AC | mass % | 0.0 | 0.2 | 0.0 | 0.2 | 0.1 | 0.1 |
| Heptane | mass % | — | — | — | — | — | — |
| HI | mass % | 0.0084 | 0.1281 | 0.0001 | 0.1290 | 0.1291 | 0.1291 |
| Other | mass % | 2.1 | 1.0 | 2.0 | 1.0 | 1.0 | 1.0 |
| Total | mass % | 100.0 | 100.0 | 100.0 | 100.0 | 100.0 | 100.0 |
| TEMPERATURE | ° C. | 14.2 | 23.2 | 23.9 | 32.2 | 23.7 | 23.7 |
| Pressure | KPaG | 127 | 121 | 121 | 122 | 121 | 121 |

| | | (11) Circulation of first absorbent | (12) Second absorption charge gas | (13) Second absorbent | (14) Second absorption offgas | (15) Bottoms liquid from second absorption column | (16) Distillate from distillation column | (17) Bottoms liquid from distillation column |
|---|---|---|---|---|---|---|---|---|
| Flow rate | Part by mass | 143.4 | 16.0 | 94.7 | 9.5 | 101.1 | 14.8 | 86.2 |
| $H_2$ | mass % | — | 0.5 | — | 0.8 | 0.0 | 0.0 | — |
| CO | mass % | — | 42.3 | — | 70.7 | 0.0 | 0.0 | — |
| $CO_2$ | mass % | — | 4.7 | — | 7.9 | 0.0 | 0.0 | — |
| $CH_4$ | mass % | — | 5.3 | — | 8.9 | 0.0 | 0.0 | — |
| $N_2$ | mass % | — | 5.7 | — | 9.5 | 0.0 | 0.0 | — |
| AD | mass % | — | 0.1 | — | 0.0 | 0.0 | 0.2 | — |
| MeI | mass % | 0.6 | 37.3 | 0.0 | 0.0 | 5.9 | 40.1 | |

TABLE 3-continued

| | | | | | | | | |
|---|---|---|---|---|---|---|---|---|
| MA | mass % | 0.3 | 1.9 | — | 0.0 | 0.3 | 2.1 | — |
| H₂O | mass % | 97.7 | 0.1 | 0.2 | 0.0 | 0.2 | 0.2 | 0.2 |
| AC | mass % | 0.2 | 0.0 | 99.1 | 0.0 | 92.8 | 56.7 | 99.0 |
| Heptane | mass % | — | — | — | — | — | — | — |
| HI | mass % | 0.1281 | 0.0001 | — | 0.0001 | 0.0000 | 0.0001 | 0.0000 |
| Other | mass % | 1.0 | 2.0 | 0.7 | 2.1 | 0.8 | 0.8 | 0.7 |
| | | | | | | | | |
| Total | mass % | 100.0 | 100.0 | 100.0 | 100.0 | 100.0 | 100.0 | 100.0 |
| TEMPERATURE | ° C. | 32.0 | 24.8 | 33.0 | 31.5 | 32.7 | 32.7 | 146.5 |
| Pressure | KPaG | 121 | 121 | 135 | 119 | 123 | 119 | 133 |

Example 1

Figure 11:
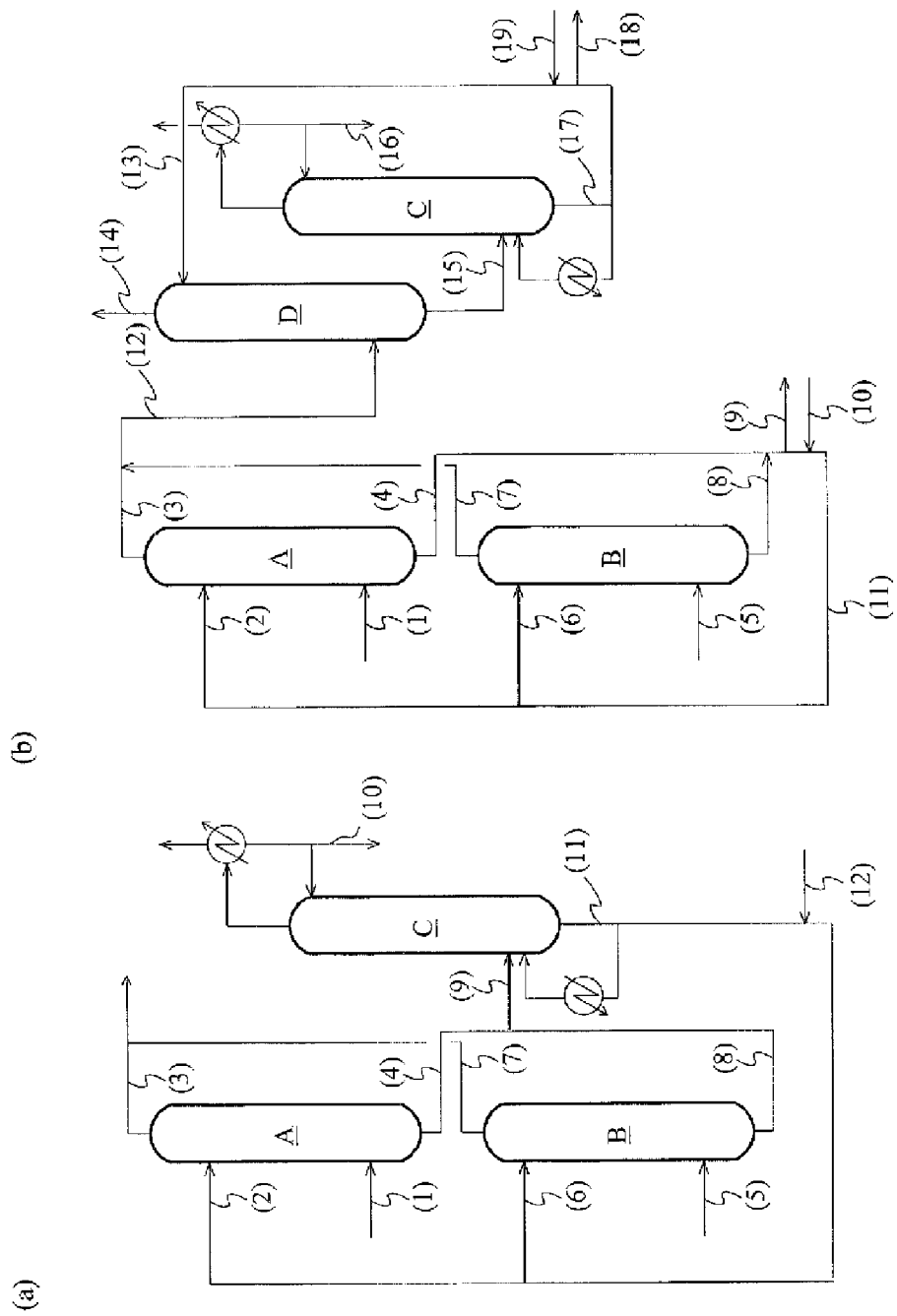
FIG. 11 is a schematic flow chart illustrating the structure of the scrubber system used in Examples and Comparative Examples.

An experiment was conducted using the scrubber system shown in FIG. 11 (b). The high-pressure charge gas (1) and the low-pressure charge gas (5) were charged into the high-pressure absorption column A (theoretical number of plates; 5) and the low-pressure absorption column B (theoretical number of plates; 5), respectively, circulating water was introduced from the tops of both absorption columns, water was sprayed from the upper portion of the absorption column with a dispersion plate to absorb the condensable gas containing an iodine compound, thus a first absorption step was performed. Then, the absorbing liquids (4) and (8) were drawn from the bottoms from the absorption column. After merging the absorbing liquids (4) and (8) from both the drawn absorption column bottoms, a portion of the absorbing liquid was withdrawn (9) and recycled to the reactor via a decanter configured to store the overhead stream condensed liquid from the low-boiling component-removing column. The high-pressure offgas (3) from the top of the high-pressure absorption column A and the low-pressure offgas (7) from the top of the low-pressure absorption column B were merged and charged into the bottom of the low-pressure absorption column D (theoretical number of plates: 5) (12), circulating heptane was introduced from the top of the low-pressure absorption column D, sprayed from the upper portion of the absorption column with a dispersion plate, the condensable gas containing an iodine compound was absorbed, thus the second absorption step was performed. Then, the absorbing liquid (15) was drawn from the absorption column bottoms. The low-pressure absorption column D bottoms liquid (15) was charged into the central portion (upper part theoretical number of plates: 2.5, lower part theoretical number of plates: 2.5) of the distillation column C (theoretical number of plates: 5) where the stripping step was performed, vapor heating was performed in the distillation column to concentrate a low boiling component other than heptane on the top of the column to produce an overhead stream (16), which was distilled off at a reflux ratio (reflux amount/distillation amount) 7 and recycled to the reactor. A solution (17) mainly containing heptane after diffusion was drawn from the distillation column bottoms, cooled, a portion of the solution (17) was discharged from the system (18), new heptane (19) was replenished, and then circulated and used as the absorbing liquid (13) of the low-pressure absorption column D. For each of the three absorption columns and the distillation column, a structured packing "Merapack 250X" (available from Thruzer Chemtech Ltd.) was used. In the present experiment, the bottoms liquid from the distillation column C was not drawn from the system. The concentration of hydrogen iodide in the bottoms liquid from the distillation column was below the detection limit. Table 4 shows the flow rates and the concentrations of various components in the above (1) to (9) and (11) to (17).

A metal test piece was placed in the bottom liquid of the distillation column C, and the above experiment was continuously performed at 133° C. for 500 hours. After the experiment was completed, the test piece was taken out and the corrosiveness was evaluated in terms of the thickness reduction rate per year using the mass change. The test piece used is the same as in Comparative Example 1. As given in Table 5, Zirconium, HC276, and SUS316 showed corrosiveness of less than 0.05 mm/Y, indicating perfect corrosion resistance, and SUS304 also had a value of 0.05 mm/Y, confirming that a SUS-based low-grade material can be used as a result of the effect according to an embodiment of the present invention. In the experiment, in addition to the test piece above, SUS304 (available from Umetoku Inc.) of the same size was placed in the bottoms liquids from the high-pressure absorption column A and the low-pressure absorption column B in the low temperature region, and an evaluation was performed; both results were the corrosiveness of less than 0.05 mm/Y indicating perfect corrosion resistance, and there was no problem with these tests.

TABLE 4

| | | (1) High-pressure charge gas | (2) High-pressure absorption column absorbing liquid | (3) High-pressure offgas | (4) High-pressure absorption column bottoms liquid | (5) Low-pressure charge gas | (6) Low-pressure absorption column absorbing liquid | (7) Low-pressure offgas | (8) Low-pressure absorption column bottoms liquid | Merged liquid of (4) and (8) |
|---|---|---|---|---|---|---|---|---|---|---|
| Flow rate | Part by mass | 1.2 | 35.8 | 1.5 | 35.5 | 16.0 | 143.1 | 15.7 | 143.4 | 178.9 |
| H₂ | mass % | 0.3 | — | 0.2 | — | 0.5 | — | 0.5 | — | — |
| CO | mass % | 67.1 | — | 53.4 | — | 42.2 | — | 43.1 | — | — |
| CO₂ | mass % | 0.9 | — | 0.7 | — | 4.7 | — | 4.8 | — | — |
| CH₄ | mass % | 3.0 | — | 2.4 | — | 5.3 | — | 5.4 | — | — |
| N₂ | mass % | 4.8 | — | 3.8 | — | 5.7 | — | 5.8 | — | — |
| AD | mass % | 0.3 | — | 0.2 | — | 0.1 | — | 0.1 | — | — |
| MeI | mass % | 21.4 | 0.6 | 16.9 | 0.6 | 37.3 | 0.6 | 33.0 | 0.6 | 0.6 |
| MA | mass % | — | 0.3 | 1.3 | 0.3 | 1.9 | 0.3 | 1.8 | 0.3 | 0.3 |

TABLE 4-continued

| | | | | | | | | | | |
|---|---|---|---|---|---|---|---|---|---|---|
| $H_2O$ | mass % | 0.1 | 97.9 | 1.0 | 98.7 | 0.1 | 97.9 | 0.0 | 97.7 | 97.9 |
| AC | mass % | 0.1 | 0.2 | 0.0 | 0.2 | 0.0 | 0.2 | 0.0 | 0.2 | 0.2 |
| Heptane | mass % | — | — | 0.0 | — | — | — | — | — | — |
| HI | mass % | 0.0111 | 0.1423 | 0.0001 | 0.1440 | 0.0084 | 0.1423 | 0.0001 | 0.1429 | 0.1431 |
| Other | mass % | 2.0 | 0.8 | 20.0 | 0.1 | 2.1 | 0.8 | 0.3 | 1.0 | 0.9 |
| Total | mass % | 100.0 | 100.0 | 100.0 | 100.0 | 100.0 | 100.0 | 100.0 | 100.0 | 100.0 |
| TEMPERATURE | °C. | 26.0 | 29.1 | 35.7 | 33.0 | 15.0 | 23.7 | 24.1 | 32.2 | — |
| Pressure | KPaG | 2760 | 2810 | 2760 | 2760 | 128 | 123 | 123 | 124 | — |

| | | (9) Extraction of first absorption bottoms | (11) Circulation of first absorbent | (12) Second absorption charge gas | (13) Second absorbent | (14) Second absorption offgas | (15) Second absorption bottoms liquid | (16) Distillate from distillation column | (17) Bottoms liquid from distillation column |
|---|---|---|---|---|---|---|---|---|---|
| Flow rate | Part by mass | 1.0 | 178.9 | 17.2 | 85.9 | 10.5 | 92.5 | 6.6 | 85.9 |
| $H_2$ | mass % | — | — | 0.5 | — | 0.8 | 0.0 | 0.0 | — |
| CO | mass % | — | — | 44.0 | — | 71.7 | 0.0 | 0.0 | — |
| $CO_2$ | mass % | — | — | 4.5 | — | 7.3 | 0.0 | 0.0 | — |
| $CH_4$ | mass % | — | — | 5.2 | — | 8.4 | 0.0 | 0.0 | — |
| $N_2$ | mass % | — | — | 5.6 | — | 9.1 | 0.0 | 0.0 | — |
| AD | mass % | — | — | 0.2 | — | 0.0 | 0.0 | 0.3 | — |
| MeI | mass % | 0.6 | 0.6 | 36.2 | 0.0 | 0.4 | 6.7 | 93.1 | — |
| MA | mass % | 0.3 | 0.3 | 1.8 | — | 0.0 | 0.3 | 4.6 | — |
| $H_2O$ | mass % | 97.9 | 97.9 | 0.1 | 0.2 | 0.1 | 0.2 | 0.2 | 0.2 |
| AC | mass % | 0.2 | 0.2 | 0.0 | 0.1 | 0.0 | 0.1 | 0.0 | 0.1 |
| Heptane | mass % | — | — | 0.0 | 99.0 | 0.0 | 91.9 | 0.0 | 99.0 |
| HI | mass % | 0.1431 | 0.1423 | 0.0001 | — | 0.0000 | 0.0000 | 0.0001 | 0.0000 |
| Other | mass % | 0.9 | 0.8 | 2.0 | 0.7 | 2.1 | 0.8 | 1.8 | 0.8 |
| Total | mass % | 100.0 | 100.0 | 100.0 | 100.0 | 100.0 | 100.0 | 100.0 | 100.0 |
| TEMPERATURE | °C. | 24.5 | 32.5 | 24.9 | 32.4 | 31.9 | 31.8 | 70.1 | 133.3 |
| Pressure | KPaG | 123 | 124 | 123 | 123 | 119 | 125 | 119 | 133 |

TABLE 5

Corrosiveness evaluation result

| | Zr | | HC276 | | SUS316 | | SUS304 | |
|---|---|---|---|---|---|---|---|---|
| | mm/y | Partial corrosion | mm/y | Partial corrosion | mm/y | Partial corrosion | mm/y | Partial corrosion |
| Comparative Example 1 | 0.00 | Absent | 0.10 | Present | 0.35 | Present | 0.42 | Present |
| Comparative Example 2 | 0.00 | Absent | 0.04 | Absent | 0.11 | Absent | 0.21 | Absent |
| Comparative Example 3 | 0.00 | Absent | 0.04 | Absent | 0.12 | Absent | 0.25 | Absent |
| Example 1 | 0.00 | Absent | 0.01 | Absent | 0.04 | Absent | 0.05 | Absent |

* Partial corrosion includes bead corrosion and pitting corrosion.

In general, the price decreases in the order of Zr>HB2>HC>SUS. Considering this, although it is affected by the wall thickness of the material, the update frequency, etc., the material can be selected based on the corrosion rate as a guideline as follows. However, this is just a guide and the initial wall thickness of the material and the update frequency can be determining factors.

Corrosion rate 0.05 mm/Y or less: Suitable for use
Corrosion rate 0.05 mm/Y over 0.1 mm/Y or less: Usable level
Corrosion rate 0.1 mm/Y over 0.2 mm/Y or less: Can be used depending on conditions
Corrosion rate over 0.2 mm/Y: Unsuitable for use

INDUSTRIAL APPLICABILITY

According to the method for producing acetic acid according to an embodiment of the present invention, acetic acid can be industrially produced by a methanol method carbonylation process (methanol method acetic acid process).

REFERENCE SIGNS LIST

1 Reactor
2 Evaporator
3, 5, 6 Distillation column
4 Decanter
7 Ion exchange resin column
8 Scrubber system
9 Acetaldehyde separation and removal system
16 Reaction mixture supply line
17 Vapor stream discharge line
18, 19 Residual liquid stream recycling line
54 Carbon monoxide-containing gas introduction line 55, 56 Potassium hydroxide introduction line
57 Catalyst circulating pump
81, 82, 83 Absorption column
84 Distillation column (stripper)
91 Distillation column (first acetaldehyde removal column)
92 Extraction column
93 Distillation column (second acetaldehyde removal column)
94 Distillation column (extraction distillation column)
95 Decanter
96 Decanter
97 Distillation column (acetaldehyde removal column)
98 Distillation column (extraction distillation column)
99 Decanter
200 Chimney tray

The invention claimed is:

1. A method, comprising:
a carbonylation reaction step of reacting methanol with carbon monoxide in the presence of: a catalytic system containing a metal catalyst and methyl iodide; acetic acid; methyl acetate; and water in a reactor to form acetic acid;
an absorption step of supplying, to an absorption column, at least a portion of offgas formed in an acetic acid production process, wherein the offgas comprises an iodine compound, bringing the offgas into contact with an absorbent containing one or more liquids selected from the group consisting of a hydrocarbon, an ester of a carboxylic acid having 3 or more carbon atoms, an ester of a carboxylic acid and an alcohol having 2 or more carbon atoms, and an ether to allow the absorbent to absorb the iodine compound in the offgas, and separating into: a gas component having a lower iodine compound concentration than the offgas; and a solution containing the absorbent and the iodine compound,
wherein the absorbent comprises a hydrocarbon.

2. A method for producing acetic acid, the method comprising:
a carbonylation reaction step of reacting methanol with carbon monoxide in the presence of: a catalytic system containing a metal catalyst and methyl iodide; acetic acid; methyl acetate;
and water in a reactor to form acetic acid;
a separation step of separating, using at least one selected from evaporators and distillation columns, a reaction mixture from the carbonylation reaction step into:
a stream including the metal catalyst;
an acetic acid stream rich in acetic acid; and
a stream richer in a low boiling component than the acetic acid stream, the method optionally further comprising (i) condensing the stream rich in a low boiling component to obtain a condensed liquid and (ii) an acetaldehyde separation and removal system that is configured to separate, using a distillation column or columns, acetaldehyde from at least a portion of the condensed liquid,
the method further comprising
an absorption step of:
supplying, to an absorption column, one or more offgas(es) selected from the group consisting of:
an exhaust gas from the reactor;
an exhaust gas from the evaporator or evaporators;
an exhaust gas from the distillation column or columns in the separation step; and
an exhaust gas from the distillation column or columns in the acetaldehyde separation and removal system;
bringing the offgas into contact with an absorbent containing one or more liquids selected from the group consisting of a hydrocarbon, an ester of a carboxylic acid having 3 or more carbon atoms, an ester of a carboxylic acid and an alcohol having 2 or more carbon atoms, and an ether to allow the absorbent to absorb an iodine compound in the offgas, and separating into:
a gas component having a lower iodine compound concentration than the offgas; and
a solution containing the absorbent and the iodine compound,
wherein the absorbent comprises a hydrocarbon.

3. A method for producing acetic acid, comprising:
a carbonylation reaction step of reacting methanol and carbon monoxide in a reactor in the presence of a catalytic system, acetic acid, methyl acetate, and water to form acetic acid, the catalytic system including a metal catalyst and methyl iodide;
an evaporation step of separating, using an evaporator, a reaction mixture from the carbonylation reaction step into:
a vapor stream; and
a residual liquid stream;
a low-boiling component-removing step of subjecting the vapor stream to distillation and separating the vapor stream into:
an overhead stream rich in a low boiling component; and
a first acetic acid stream rich in acetic acid; and
a dehydration step of subjecting the first acetic acid stream to distillation and separating the first acetic acid stream into:
an overhead stream rich in water; and
a second acetic acid stream richer in acetic acid than the first acetic acid stream,
the method optionally further comprising:
a high-boiling component-removing step of distilling the second acetic acid stream and separating the second acetic acid stream into:
a bottoms stream rich in high boiling components; and
a third acetic acid stream richer in acetic acid than the acetic acid stream before being subjected to the distillation; and/or
(i) condensing the stream rich in a low boiling component to obtain a condensed liquid and (ii) an acetaldehyde separation and removal system that is configured to separate, using a distillation column or columns, acetaldehyde from at least a portion of the condensed liquid,
the method further comprising:
an absorption step of supplying, to an absorption column, one or more offgas(es) selected from the group consisting of:
an exhaust gas from the reactor;
an exhaust gas from the evaporator;
an exhaust gas from the distillation column in the low-boiling component-removing step;
an exhaust gas from the distillation column in the dehydration step;
an exhaust gas from the distillation column in the high-boiling component-removing step; and
an exhaust gas from the distillation column in the acetaldehyde separation and removal system;
bringing the offgas into contact with an absorbent containing one or more liquids selected from the group consisting of a hydrocarbon, an ester of a carboxylic acid having 3 or more carbon atoms, an ester of a carboxylic acid and an alcohol having 2 or more carbon atoms, and an ether to allow the absorbent to absorb an iodine compound in the offgas; and separating into:

a gas component having a lower iodine compound concentration than the offgas; and a solution containing the absorbent and the iodine compound, wherein the absorbent comprises a hydrocarbon.

4. The method according to claim 1, wherein a concentration of the one or more liquids selected from the group consisting of a hydrocarbon, an ester of a carboxylic acid having 3 or more carbon atoms, an ester of a carboxylic acid and an alcohol having 2 or more carbon atoms, and an ether in the absorbent is 10 ppm by mass or greater.

5. The method according to claim 1, wherein the acetic acid production process comprises:

a first absorption step of supplying at least a portion of offgas formed in the process to an absorption column and bringing the portion of the offgas into contact with a first absorbent to allow the first absorbent to absorb an iodine compound in the offgas, and separating into:

a first gas component having a lower iodine compound concentration than the offgas; and a first solution containing the first absorbent and the iodine compound; and a second absorption step of, in an absorption column, bringing the first gas component into contact with a second absorbent to allow the second absorbent to absorb an iodine compound in the first gas component, the second absorbent having a composition different from that of the first absorbent, and separating into:

a second gas component having a lower iodine compound concentration than the first gas component; and a second solution containing the second absorbent and an iodine compound, the method comprising, as the first absorption step and/or the second absorption step, the absorption step using an absorbent containing one or more liquids selected from the group consisting of a hydrocarbon, an ester of a carboxylic acid having 3 or more carbon atoms, an ester of a carboxylic acid and an alcohol having 2 or more carbon atoms, and an ether, wherein the absorbent comprises a hydrocarbon.

6. The method according to claim 5, wherein the first absorbent comprises water.

7. The method according to claim 5, wherein the second absorption step is the absorption step using an absorbent containing one or more liquids selected from the group consisting of a hydrocarbon, an ester of a carboxylic acid having 3 or more carbon atoms, an ester of a carboxylic acid with an alcohol having 2 or more carbon atoms, and an ether.

8. The method according to claim 5, wherein the first or second absorbent comprises water in a concentration of 10 ppm or greater.

9. The method according to claim 5, wherein, the first or second absorbent comprises water in a concentration of 10 ppm or greater, and a concentration of the one or more liquids selected from the group consisting of a hydrocarbon, an ester of a carboxylic acid having 3 or more carbon atoms, an ester of a carboxylic acid and an alcohol having 2 or more carbon atoms, and an ether in the other one of the first absorbent and the second absorbent is 10 ppm by mass or greater.

10. The method according to claim 5, wherein the first absorption step and the second absorption step are performed using different absorption columns.

11. The method according to claim 1, further comprising a stripping step of subjecting a solution containing an absorbent and an iodine compound to distillation, wherein the iodine compound comprises methyl iodide, the absorbent containing the one or more liquids selected from the group consisting of a hydrocarbon, an ester of a carboxylic acid having 3 or more carbon atoms, an ester of a carboxylic acid and an alcohol having 2 or more carbon atoms, and an ether, and separating into:

an overhead stream rich in methyl iodide; and a bottoms stream rich in the liquid.

12. The method according to claim 11, wherein the overhead stream rich in methyl iodide is recycled to the reaction step.

13. The method according to claim 11, wherein a methyl iodide concentration in a charge liquid to a distillation column in the stripping step is 1 ppm by mass or greater.

14. The method according to claim 11, wherein a charge liquid in the distillation column performing the stripping step comprises hydrogen iodide and the concentration of hydrogen iodide in the charge liquid is less than 1 mass %.

* * * * *